US012187891B2

(12) United States Patent
Ichikawa et al.

(10) Patent No.: US 12,187,891 B2
(45) Date of Patent: Jan. 7, 2025

(54) ALKYLENE OXIDE DERIVATIVE, DEFOAMING AGENT, LUBRICANT, COSMETIC BASE MATERIAL AND COSMETICS CONTAINING SAME, HAIR CLEANING AGENT COMPOSITION, AND BODY CLEANING AGENT COMPOSITION

(71) Applicant: NOF CORPORATION, Tokyo (JP)

(72) Inventors: Shoko Ichikawa, Kawasaki (JP); Yusuke Hara, Yokohama (JP); Kazuki Sunada, Tokyo (JP); Koji Sekiguchi, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 779 days.

(21) Appl. No.: 17/424,039

(22) PCT Filed: Jan. 16, 2020

(86) PCT No.: PCT/JP2020/001252
§ 371 (c)(1),
(2) Date: Jul. 19, 2021

(87) PCT Pub. No.: WO2020/153223
PCT Pub. Date: Jul. 30, 2020

(65) Prior Publication Data
US 2022/0089869 A1    Mar. 24, 2022

(30) Foreign Application Priority Data

Jan. 21, 2019  (JP) .............................. 2019-007867
Sep. 25, 2019  (JP) .............................. 2019-173711
Oct. 2, 2019   (JP) .............................. 2019-181820

(51) Int. Cl.
| | |
|---|---|
| C08L 71/02 | (2006.01) |
| A61K 8/39 | (2006.01) |
| A61K 8/86 | (2006.01) |
| A61Q 1/14 | (2006.01) |
| A61Q 5/00 | (2006.01) |
| A61Q 5/02 | (2006.01) |
| A61Q 19/00 | (2006.01) |
| A61Q 19/10 | (2006.01) |
| C08G 65/02 | (2006.01) |
| C08G 65/26 | (2006.01) |
| C10M 145/26 | (2006.01) |
| C10M 145/38 | (2006.01) |
| C10M 173/02 | (2006.01) |

(Continued)

(52) U.S. Cl.
CPC ............... *C08L 71/02* (2013.01); *A61K 8/39* (2013.01); *A61K 8/86* (2013.01); *A61Q 5/00* (2013.01); *A61Q 19/00* (2013.01); *C08G 65/02* (2013.01); *C08G 65/2609* (2013.01); *C10M 145/26* (2013.01); *C10M 145/38* (2013.01); *C10M 173/02* (2013.01); *A61Q 1/14* (2013.01); *A61Q 5/02* (2013.01); *A61Q 19/10* (2013.01); *C08G 65/2663* (2013.01); *C08G 2650/58* (2013.01); *C10M 2209/104* (2013.01); *C10M 2209/105* (2013.01); *C10M 2209/108* (2013.01); *C10N 2030/06* (2013.01); *C10N 2030/18* (2013.01); *C10N 2040/08* (2013.01); *C10N 2040/20* (2013.01)

(58) Field of Classification Search
CPC ............ C08L 71/02; A61K 8/86; A61K 8/39; C10M 145/26; C10M 145/38; C10M 173/02; C10M 2209/104; C10M 2209/105; C10M 2209/108; A61Q 5/02; A61Q 19/10; A61Q 1/14; A61Q 5/00; A61Q 19/00; C08G 65/2663; C08G 2650/58; C08G 65/2609; C08G 65/02; C10N 2030/06; C10N 2030/18; C10N 2040/08; C10N 2040/20
See application file for complete search history.

(56) References Cited

U.S. PATENT DOCUMENTS

| | | | |
|---|---|---|---|
| 5,066,763 A | 11/1991 | Andre et al. | |
| 6,617,419 B1 | 9/2003 | Hofmann et al. | |

(Continued)

FOREIGN PATENT DOCUMENTS

| | | |
|---|---|---|
| JP | 03-043416 A | 2/1991 |
| JP | 08-231977 A | 9/1996 |

(Continued)

OTHER PUBLICATIONS

International Search Report for PCT/JP2020/001252 dated Mar. 24, 2020 [PCT/ISA/210].
Extended European Search Report dated Sep. 14, 2022 in European Application No. 20745888.6.
Reporting Letter of the Extended European Search Report dated Sep. 21, 2022 in European Application No. 20745888.6.

*Primary Examiner* — Rabon A Sergent
(74) *Attorney, Agent, or Firm* — Sughrue Mion, PLLC

(57) ABSTRACT

An alkylene oxide derivative represented by formula (1), wherein a ratio Mz/Mw of a weight average molecular weight (Mw) and z average molecular weight (Mz) calculated from a chromatogram obtained by gel permeation chromatography measurement of the alkylene oxide derivative satisfies formula (2) below:

$$Z-[O-(PO)_a-(PO)_b/(EO)_c]-H]_n \qquad (1)$$

$$5 \leq M_z/M_w \leq 60 \qquad (2)$$

where Z, n, PO, EO, a, b and c are as defined herein; a+b+c≥10, and b/c=1/5~5/1; $(PO)_b/(EO)_c$ indicates that PO and EO are randomly added; and a random ratio x of PO and EO satisfies 0.1≤x≤1.

10 Claims, 2 Drawing Sheets

(51) Int. Cl.
    *C10N 30/06*     (2006.01)
    *C10N 30/18*     (2006.01)
    *C10N 40/08*     (2006.01)
    *C10N 40/20*     (2006.01)

(56) References Cited

U.S. PATENT DOCUMENTS

| | | |
|---|---|---|
| 2016/0263009 A1 | 9/2016 | Saito et al. |
| 2020/0190260 A1 | 6/2020 | Hara et al. |
| 2020/0207911 A1 | 7/2020 | Murai et al. |

FOREIGN PATENT DOCUMENTS

| | | |
|---|---|---|
| JP | 2002-543228 A | 12/2002 |
| JP | 2006-241412 A | 9/2006 |
| JP | 2009-067694 A | 4/2009 |
| JP | 2012-131982 A | 7/2012 |
| JP | 2013-241581 A | 12/2013 |
| JP | 2015-096247 A | 5/2015 |
| JP | 2015-096477 A | 5/2015 |
| JP | 2015-098452 A | 5/2015 |
| JP | 2015-120661 A | 7/2015 |
| JP | 2017-137254 A | 8/2017 |
| WO | 2018/030283 A1 | 2/2018 |
| WO | 2018/221278 A1 | 12/2018 |

ALKYLENE OXIDE DERIVATIVE, DEFOAMING AGENT, LUBRICANT, COSMETIC BASE MATERIAL AND COSMETICS CONTAINING SAME, HAIR CLEANING AGENT COMPOSITION, AND BODY CLEANING AGENT COMPOSITION

CROSS REFERENCE TO RELATED APPLICATIONS

This application is a National Stage of International Application No. PCT/JP2020/001252 filed Jan. 16, 2020, claiming priority based on Japanese Patent Application No. 2019-007867 filed Jan. 21, 2019, Japanese Patent Application No. 2019-173711 filed Sep. 25, 2019 and Japanese Patent Application No. 2019-181820 filed Oct. 2, 2019.

TECHNICAL FIELD

The present invention relates to a novel alkylene oxide derivative which can be effectively used for various kinds of applications including an antifoaming agent, lubricant, cosmetic base material and cosmetics containing the same.

BACKGROUND ARTS

An alkylene oxide derivative is generally produced by ring-opening addition polymerization of oxyethylene (EO), oxypropylene (PO) and the like. As the balance of hydrophilic and lipophilic properties and molecular weight can be controlled by controlling the addition molar number and addition pattern of EO, PO and the like, it has been used for various kinds of applications including an oily agent, polymer material, dispersing agent, surfactant and the like. As the dispersing property of water and water solubility of the random addition product of EO and PO can be adjusted by the addition molar numbers of EO and PO, it has been used for aqueous type antifoaming agent, lubricant, cosmetic base material or the like.

Aqueous antifoaming agents have been used in various fields such as pulp and paper manufacturing industry, paint manufacturing industry, cement manufacturing industry, fiber processing industry, fermentation industry, waste water or the like. It is thus demanded an antifoaming agent which can be used in a wide range of temperature of, for example, outer atmosphere in summer to winter in the application of cement, about 40° C. in the fermentation application, and 50° C. or higher in the fiber processing application. As the antifoaming agent, it has been known oil-in water type emulsion whose main component is silicone oil or higher alcohol. However, in the case that the emulsion type antifoaming agent is used for a long time, the sedimentation and uneven distribution of the antifoaming agent tend to occur, resulting in problems that the antifoaming property is gradually diminished over time and that sedimentation product is generated to contaminate facilities and products.

Further, it has been used polyalkylene glycol-based antifoaming agent as the antifoaming agent having good dispersion in water. For example, in patent document 1, it is reported that aqueous type antifoaming agent, containing alkylene oxide derivative having a higher alcohol with EO and PO added in random or block addition mode, exhibits good antifoaming property with respect to a commonly applied foaming agent.

In the field of working oils or the like of lubricating agents, alkylene oxide having high cooling efficiency has been widely used, as it is inflammable, high in stability at high temperature and free from possibility of separation and corruption. For example, in patent document 2, an alkylene oxide addition product of a diol is reported as a lubricating base oil excellent in water solubility and lubricating property.

Therefore, for example in patent document 3, as a lubricating agent having antifoaming property, it is disclosed a metal process oil composition containing polyether of reverse block type in which oxypropylene is added to polyethylene glycol.

Further, in cosmetic bases, for example hair cosmetics, solid solders, oils and fats or film-forming polymers are often used, for improving styling performance, which means preserving capability of setting of hair style. According to a hair-styling composition containing solders or oils and fats which are solid at room temperature, extension of the hair styling composition during the hair styling is poor and the hair becomes sticky after the hair styling, resulting in problems. According to the hair styling composition containing the film-forming polymer, the problems of the extension or stickiness can be reduced. As the film is formed on the surface of hair after the hair styling provided by the film-forming polymer, the styled hair becomes hard resulting in the feeling of stiffness. An alkylene oxide derivative is used for controlling the feeling, for removing the stiffness.

For example, it is reported, in patent document 4, that an alkylene oxide derivative and film-forming high polymer are mixed to form a uniform and transparent film on hairs and to provide a cosmetic free from the sticky feeling and stiffness and having sufficient hair styling and re-hair styling performances.

As a hair styling composition without the film-forming polymer added, patent document 5 discloses that an emulsion hair styling composition obtained by mixing an alkylene oxide derivative, oily agent and water is free from creaky feeling and has cohesiveness of hairs and styling performance.

Further, a skin cosmetic is used for assisting barrier function and water preserving function of stratum corneum, which are functions originally possessed by skin. Generally, as skin care by a skin cosmetic, methods of supplying water through a toner and using a cosmetic blended with an oily component such as emulsion or cream are listed. It is demanded for the skin cosmetic the moisture preserving effect as well as good feeling in use upon applying on the skin surface. It is thus proposed a cosmetic having compatibility with skin upon application and thick feeling. Further, recently, for enhancing blood flow and feeling better skin care effects, there are users using the skin cosmetic while massage is performed. For example, according to patent document 6, it is proposed a cosmetic having thickness in liquid feeling during massage, good extension and reduced slimy feeling and obtained by blending a sugar alcohol, polyether-denatured silicone and water-soluble polymer.

Recently, the hair cleansing agent is commercialiized after added values are improved, including smoothness during the rinsing and moisture preserving property in addition to the cleansing power of removing contamination of sebum.

As the method of improving the added values, it is known the method of adding a moisture preserving agent or emollient (oily component). For example, according to patent document 7, a specific polyalkylene glycol derivative is blended into a cleansing agent to improve the foaming performance and bubble quality and to reduce the creakiness during the rinsing.

Further, it has been tried to develop products in which the cohesiveness of hairs after drying as well as the cleansing and rinsing are improved and in which the effect of cohesiveness of the hairs is sustained. According to patent document 8, it is reported a hair cleansing agent in which bedhead is prevented and cohesiveness or smoothness and softness preferred in feeling are imparted to hairs, by blending a specific high molecular weight component, polyalkylene glycol derivative, anionic surfactant and cationic polymer.

Recently, the body cleansing agent is commercialized by improving added values such as smoothness during the rinsing and moisture-preserving feeling, in addition to cleansing power of removing contamination by sebum.

As the method of improving the added value of the body cleansing agent, it is known the method of adding a moisture preserving agent or emollient agent (oily component). For example, according to patent document 9, it is reported a cleanser composition in which good bubble quality and feeling during the rinsing are obtained, the tightening of skin after drying is prevented and stability over time and recovery from storing at low temperature are excellent, by combining a specific glycerin derivative and surfactant at a specific ratio.

Further, it has been tried to develop products in which the effect of preserving moisture is sustained. According to patent document 10, it is reported a cleanser composition in which smoothness of skin and moisture feeling are improved and tightness of skin after repeated use is prevented, by mixing polyoxypropylene diglyceryl ether, polyether-denatured silicone and cationic polymer.

PRIOR TECHNICAL DOCUMENTS

Patent Document (Patent document 1) Japanese patent publication No. 2015-096247A
(Patent document 2) Japanese patent publication No. 2012-131982A
(Patent document 3) Japanese patent publication No. H08-231977A
(Patent document 4) Japanese patent publication No. 2015-096477A
(Patent document 5) Japanese patent publication No. 2015-120661A
(Patent document 6) Japanese patent publication No. 2015-98452A
(Patent document 7) Japanese patent publication No. 2006-241412A
(Patent document 8) Japanese patent publication No. 2017-137254A
(Patent document 9) Japanese patent publication No. 2006-241412A
(Patent document 10) Japanese patent document No. 2009-67694A

SUMMARY OF THE INVENTION

Object to be Solved by the Invention

However, according to the antifoaming agent described in patent document 1, temperature dependence is observed in the antifoaming performance, and it may be necessary to change the antifoaming agent depending on applications, steps and seasons.

According to the lubricating agent of patent document 2, in the case that the surfactant such as alkylene oxide is used, the generation of bubbles may be considerable, the lubrication may be defective and the workability may be deteriorated, which are problematic.

According to the lubricating agent described in patent document 3, in the case that the lubricating agent is heated to a high temperature of 50° C. or higher due to processing heat upon use, bubbles are generated in the lubricating agent so that it is difficult to obtain the lubricating and antifoaming property.

According to patent document 4, the texture of hair after the styling is hardened, so that is difficult to complete the styling while the good finger passage and softness of the texture are maintained.

According to patent document 5, in the case that the hair is under a high humidity such as in rainy day or dried by heat supplied by a drier or hair iron, there is the problem that the cohesiveness is deteriorated.

According to patent document 6, in the case that massage is performed strongly for obtaining high skin care effect, friction feeling may be provided on the skin.

Further, in the market of a cosmetic and toiletries, interest is growing about care of odor such as tabaco odor and cooking odor including that of grilled meat. As the method of suppressing the attached odor, it is known the method of utilizing the odor adsorption capability of carbon or the like or of masking by perfume or the like. However, the preference of kinds and strength of the odor is different depending on persons, and one may prefer strong odor and another may prefer no perfume or fine perfume. In the case that the effect of suppressing the odor is imparted to the cleansing agent itself, one preferring no perfume or fine perfume can select the strength of perfume which the one prefers. However, in the case that an amount of a perfume added to the cleansing agent is reduced responsive to such demand, the effect of suppressing the added odor is reduced so that the added odor cannot be suppressed.

It is thus demanded a hair cleansing agent in which the feeling during the rinsing is smooth, the cohesiveness of hair is sustained after the cleansing and the tabaco odor and cooking odor can be suppressed.

Further, based on such circumstances, it is demanded a body cleanser composition in which the feeling during the rinsing is smooth, the moisture feeling of skin is sustained after the cleansing and the tabaco odor and cooking odor can be suppressed.

An object of the present invention is to provide an alkylene oxide derivative containing a high molecular weight body and suitable for various applications including an antifoaming agent, lubricating agent, cosmetic base, cosmetic composition containing the same and the like.

Further, an object of the present invention is to provide an antifoaming agent having sufficiently high antifoaming property regardless of temperature by containing the alkylene oxide derivative containing the high molecular weight body.

Further, an object of the present invention is to provide a lubricating agent having both of sufficient lubricating property and antifoaming property, by incorporating the alkylene oxide derivative containing the high molecular weight body.

Further, an object of the present invention is to provide a hair cosmetic excellent in styling performance, cohesiveness and finger passage after the styling and softness of texture, by the alkylene oxide derivative containing the high molecular weight body.

Further, an object of the present invention is to provide a skin cosmetic having good compatibility with skin upon application, good feeling of thickness and reduced feeling of friction during massage, by the alkylene oxide derivative containing the high molecular weight body.

Further, an object of the present invention is to provide a hair cleanser composition having smooth feeling during the rinsing, cohesiveness of hair after the cleansing and capability of suppressing tabaco odor and cooking odor.

Further, an object of the present invention is to provide a body cleanser composition, in which the feeling during the rinsing is smooth, moisture feeling of skin is sustained after the cleansing and tabaco odor and cooking odor can be suppressed.

Solution for the Object

As the result of extensive research based on the items described above, the inventors found that the objects described above can be solved by a novel alkyl oxide derivative, suitable for various kinds of applications, whose molecular weight pattern obtained from gel permeation chromatography measurement is unsymmetrical in right and left sides and whose molecular weight distribution is deviated on the side of a higher molecular weight.

That is, the present inventions are as follows.

(1) An alkylene oxide derivative represented by formula (1), wherein a ratio Mz/Mw of a weight average molecular weight (Mw) and z average molecular weight (Mz) calculated from a chromatogram obtained by gel permeation chromatography measurement of the alkylene oxide derivative satisfies formula (2) below.

$$Z - [O - (PO)_a - (PO)_b / (EO)_c] - H]_n \quad (1)$$

(in the formula (1),

Z represents a residual group of a compound having a number of carbons of 1 to 24 and 1 to 6 hydroxyl groups wherein all the hydroxyl groups are excluded,
n represents a number of 1 to 6,
PO represents oxypropylene group,
EO represents oxyethylene group,
a and b represent numbers of moles added of the oxypropylene group PO, respectively,
c represents a number of moles added of the oxyethylene group EO,
a represents a number of 1 to 100, b represents a number of 1 to 100, c represents a number of 1 to 200, a+b+c≥10, and b/c=1/5~5/1,
$(PO)_b/(EO)_c$ indicates that the oxypropylene group PO and oxyethylene group EO are randomly added, and
a random ratio x of the oxypropylene group PO and oxyethylene group EO satisfies 0.1≤x≤1.)

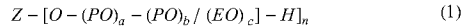

$$5 \leq M_z / M_w \leq 60 \quad (2)$$

(2) The alkylene oxide derivative of (1), wherein a tailing coefficient (TF) calculated from the chromatogram satisfies formulas (3) and (4).

$$TF = W_{0.05L} / 2A \quad (3)$$

$$1.5 \leq TF \leq 5.0 \quad (4)$$

An intensity of a refractive index is L/20 on the chromatogram at two points R and S, L is assigned to a length of a perpendicular line drawn from a maximum point K whose intensity of a refractive index on the chromatogram takes a maximum value to a base line B on the chromatogram, an elution time at the point R is shorter than an elution time at the point S, T is assigned to a crossing point of a straight line H connecting the point R and the point S and of the perpendicular line drawn from the maximum point K, to the base line B, A is assigned to a distance between the point S and the crossing point T, and $W_{0.05L}$ is assigned to a distance between the point R and the point S.

(3) The alkylene oxide derivative of (1) or (2), wherein the random ratio x satisfies 0.5≤x≤1.

(4) An antifoaming agent comprising the alkylene oxide derivative of any one of (1) to (3).

(5) A lubricant comprising the alkylene oxide derivative of any one of (1) to (3).

(6) A cosmetic base material comprising the alkylene oxide derivative of any one of (1) to (3).

(7) A hair cosmetic comprising the cosmetic base material of (6).

(8) A skin cosmetic comprising the cosmetic base material of (6).

(9) A hair cleanser composition comprising 0.01 to 20 mass % of (A) the alkylene oxide derivative of any one of (1) to (3), 1 to 50 mass % of (B) an anionic surfactant, and 0.01 to 3 mass % of (C) a cationic polymer.

(10) A body cleanser composition comprising 0.01 to 20 mass % of (A) the alkylene oxide derivative of any one of (1) to (3), 0.1 to 50 mass % of (D) an anionic surfactant, and 0.5 to 50 mass % of (E) a polyhydric alcohol.

Effects of the Invention

According to the present invention, it is possible to provide a novel alkyl oxide derivative whose molecular weight distribution is deviated on the side of higher molecular weight and suitable for various kinds of applications.

Further, according to the antifoaming agent composed of the alkylene oxide derivative of the present invention, it is possible to obtain sufficient antifoaming property irrespective of temperature.

Further, according to the lubricating agent composed of the alkylene oxide derivative of the present invention, it is possible to reduce the friction coefficient between adjacent and contacting bodies.

Further, according to the hair cosmetic composed of the alkylene oxide derivative of the present invention, it is possible to provide the hair cosmetic excellent in styling performance, cohesiveness and finger passage after the styling and softness of texture.

Further, according to the skin cosmetic composed of the alkylene oxide derivative of the present invention, it is possible to provide the skin cosmetic having good compatibility with skin upon application, feeling of thickness and reduced feeling of friction during massage, by the alkylene oxide derivative containing the high molecular weight body.

Further, by blending the novel alkylene oxide derivative of the present invention into a hair cleanser composition, it is possible to obtain the hair cleanser composition having smooth feeling during the rinsing, sustained cohesiveness of hair after the cleansing and suppressed tabaco odor and cooking odor.

Further, by blending the novel alkyl oxide derivative of the present invention into a body cleanser composition, it is possible to obtain the body cleanser composition having smooth feeling during the rinsing, sustained moisture feeling after the cleansing and suppressed tabaco odor and cooking odor.

MODES FOR CARRYING OUT THE INVENTION

Figure 1:
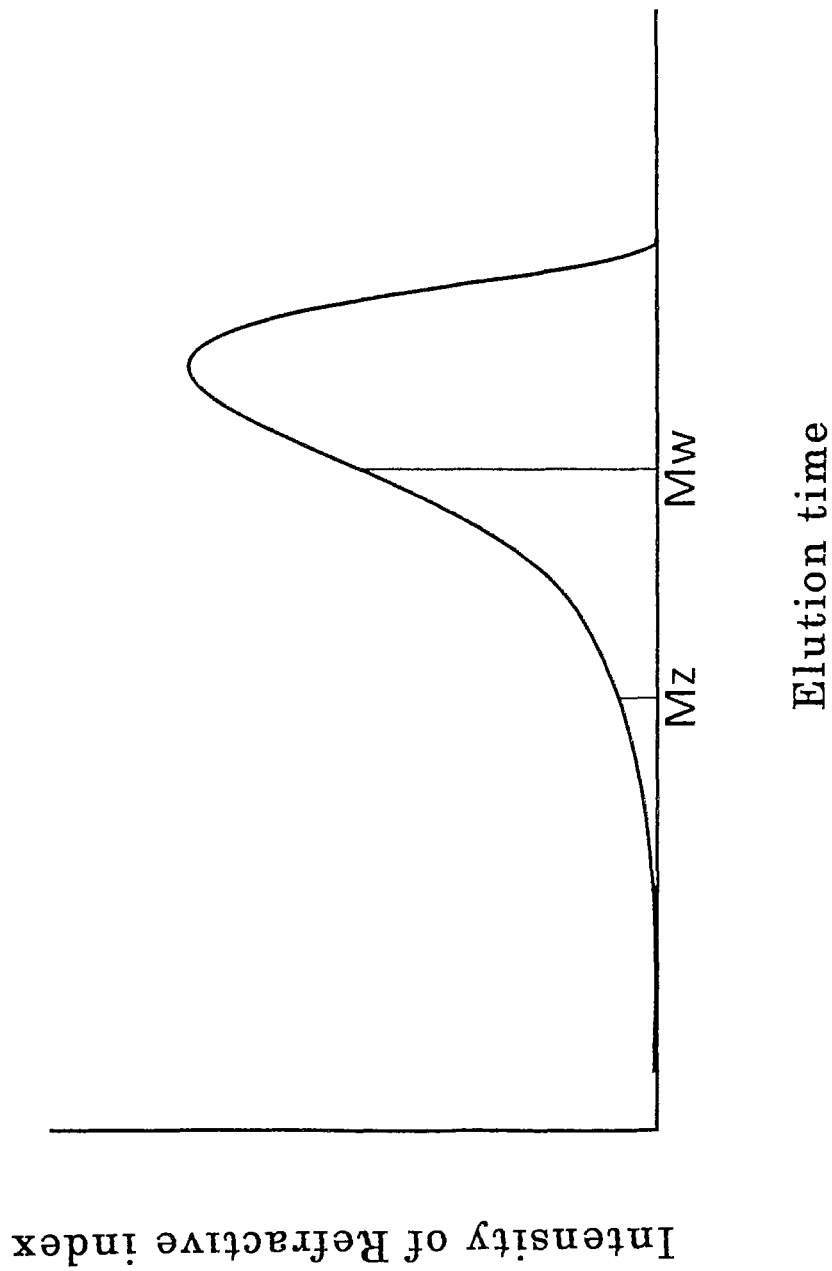
FIG. 1 is a model chromatogram for illustrating Mz/Mw defined by the present invention.

The numeral range defined in the specification using a symbol of "to" includes numerical values (upper and lower limits) at both ends of "to". For example, "2 to 5" means 2 or larger and 5 or smaller.
(Alkylene Oxide Derivative)

The alkylene oxide derivative of the present invention is a compound shown by the formula (1).

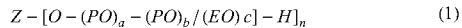

$$Z-[O-(PO)_a-(PO)_b/(EO)c]-H]_n \quad (1)$$

In the formula (1), Z represents a residual group of a compound having a number of carbons of 1 to 24, preferably of 1 to 12, more preferably of 1 to 6 and having 1 to 6 hydroxyl groups in which all the hydroxyl groups are excluded, and n represents a number of the hydroxyl groups of the compound Z. The compound (Z(OH)n) having 1 to 6 hydroxyl groups includes methanol, ethanol and butanol in the case of n=1, ethylene glycol, propylene glycol and hexylene glycol in the case of n=2, glycerin and trimethylolpropane in the case of n=3, erythritol, pentaerythritol, sorbitan, diglycerin and alkyl glycoside in the case of n=4, xylitol in the case of n=5, and dipentaerythritol, sorbitol and inositol in the case of n=6. Further, the mixtures thereof may be used as the compound having 1 to 6 hydroxyl group. n may preferably be 1 to 4 and most preferably be 1 to 3.

In the formula (1), Z may be $R^1$, and n=1 in this case. In this case, $R^1$ represents a hydrocarbon group having a carbon number of 1 to 24. The hydrocarbon group having a carbon number of 1 to 24 is a functional group composed of carbon and hydrogen, may be one selected from alkyl group, alkenyl group, cycloalkyl group, aryl group or aralkyl group, may preferably be alkyl group or alkenyl group, more preferably be alkyl group or alkenyl group having a carbon number of 1 to 12, and most preferably be alkyl group having a carbon number of 1 to 6. The alkyl group having a carbon number of 1 to 6 may be that of a straight chain or branched chain, and preferably be that of a straight chain. The straight chain alkyl group having a carbon number of 1 to 6 includes methyl group, ethyl group, propyl group, butyl group hexyl group or the like, for example. The hydrocarbon group having a number of carbons of 1 to 24 may be used alone or in combination of two or more.

PO represents oxypropylene group, EO represents oxyethylene group and a and b represent the number of moles added of PO and EO, respectively. "a" represents a number of 1 to 100, b represents a number of 1 to 100, c represents 1 to 200, and a+b+c≥10. $(PO)_b/(EO)_c$ represents polyoxyalkylene group in which PO and EO are randomly added, a molar ratio (b/c) of PO and EO is 1/5 to 5/1, and the random ratio x of PO and EO satisfies 0.1≤x≤1.

In the case that a+b+c is lower than 10, the versatility of the temperature of the antifoaming agent, lubricating property of the lubricant or styling performance of the hair cosmetic may possibly be insufficient, the durability of ruly style and the effect of suppressing tabaco odor and cooking odor may possible by insufficient in the case of the hair cleansing composition, and the durability of moisture feeling and effect of suppressing tabaco odor and cooking odor may possibly be insufficient in the case of the body cleansing agent. On the viewpoint, a+b+c is made 10 or larger and more preferably be 15 or larger. Further, as a+b+c is larger, the viscosity is increased. On the viewpoint of ease of dispersion and blending, a+b+c may preferably be 150 or smaller, more preferably be 120 or smaller and most preferably be 100 or smaller.

Further, the total molar number n×(a+b+c) of PO and EO added may preferably be 30 or larger, more preferably be 40 or larger, still more preferably be 50 or larger, and most preferably be 55 or larger. Further, it may preferably be 120 or smaller, more preferably be 100 or smaller and most preferably be 80 or smaller.

In the case that b/c is smaller than 1/5, the versatility of temperature of the antifoaming agent or lubricating property of the lubricant may possible by deteriorated, and the hair cosmetic may by sticky to deteriorate the finger passage. In the case that it exceeds 5/1. The dispersing property and solubility in water may possibly be deteriorated.

In the case of the hair cleanser composition having b/c smaller than 1/5, the rinsing property of the cleanser may possibly be deteriorated. In the case that it is larger than 5/1, the dispersing property and solubility in water may possibly be deteriorated.

In the case of the body cleanser composition having b/c smaller than 1/5, the rinsing property of the cleanser may possibly be deteriorated. In the case that it is larger than 5/1, the solubility in water may possibly be deteriorated.

The random ratio x of PO and EO is calculated based on formula (5).

$$x = (b+c)/(a+b+c) \quad (5)$$

The random ratio x satisfies 0.1≤x≤1. In the case that the random ratio x is smaller than 0.1, as the versatility of temperature of the antifoaming agent, lubricating property of the lubricant or styling performance of the hair cosmetic may possibly be deteriorated, it is 0.1 or larger, may preferably 0.5 or larger, more preferably be 0.6 or larger and most preferably be 0.8 or larger. Further, the random ratio x is 1 or smaller, it may preferably satisfy x<1, may preferably be 0.99 or smaller, and most preferably be 0.97 or smaller.

In the case of the hair cleanser composition, the random ratio x satisfies 0.1≤x≤1. In the case that the random ratio x is smaller than 0.1, the durability of the ruly style and the effect of suppressing the tabaco odor and cooking odor may possibly be insufficient. It is thus 0.1 or larger, preferably 0.6 or larger, more preferably 0.7 or larger and most preferably 0.8 or larger. Further, the random ratio x is 1 or smaller, it may preferably satisfy x<1, more preferably be 0.99 or smaller and most preferably 0.97 or smaller.

In the case of the body cleanser composition, the random ratio x satisfies 0.1≤x≤1. In the case that the random ratio x is smaller than 0.1, the durability of moisture feeling or the effect of suppressing tabaco odor and cooking odor may possibly be insufficient. It is thus 0.1 or larger, preferably 0.5 or larger, more preferably 0.6 or larger and most preferably 0.8 or larger. Further, the random ratio is 1 or smaller, may preferably satisfy x<1, preferably be 0.99 or smaller and most preferably be 0.97 or smaller.

(GPC Characteristics of Alkylene Oxide Derivative)

The alkylene oxide derivative of the present invention is defined by molecular weights obtained by a chromatogram obtained by using a differential refractometer in gel permeation chromatography (GPC). The chromatogram is a graph showing the relationship between the intensity of refractive index and elution time.

According to the derivative of the present invention, the ratio (Mz/Mw) of the weight average molecular weight (Mw) and z average molecular weight (Mz) obtained by the chromatogram satisfies 5≤Mz/Mw≤60.

The method of calculating Mz/Mw will be described further, referring to the model diagram of the chromatogram of FIG. 1. The horizontal axis indicates the elution time and vertical axis indicates the intensity of refractive index obtained by the differential diffractometer. In the case that a sample solution is injected into and developed in a gel permeation chromatograph, the elution of molecules having the highest molecular weight is initiated first, and the elution curve is raised as an increase of the intensity of the refractive index. Thereafter, the elution curve goes down from the maximum point where the intensity of the refractive index takes the maximum value.

Here, Mw and Mz are calculated from the GPC based on the following formulas.

$$Mw = \frac{\sum (M^2 \cdot N)}{\sum (M \cdot N)} = \frac{\sum (C \cdot M)}{\sum (C \cdot M)} \tag{6}$$

$$Mz = \frac{\sum (M^3 \cdot N)}{\sum (M^2 \cdot N)} = \frac{\sum (C \cdot M^2)}{\sum (C \cdot M)} \tag{7}$$

Further, N represents a number of polymer molecules, M represents a molecular weight and C represents a concentration of a sample. Mw represents a weighted average by applying the molecular weight as a weight, and Mz represents a weighted average by applying the square of the molecular weight as a weight. Mw is affected by the presence of high molecular weight bodies, and Mz is more affected by the presence of the high molecular weight bodies than Mw. Thus, according to the alkylene oxide derivative of the present invention, Mw and Mz are obtained shown in the chromatogram as shown in FIG. 1.

As Mz/Mw is smaller than 5, the versatility of temperature of the antifoaming agent, lubricating property of the lubricant and the styling performance of the hair cosmetic may possibly be insufficient. On the viewpoint, Mz/Mw may preferably be 5 or larger, more preferably be 10 or larger, still more preferably be 20 or larger, and most preferably be 25 or larger. In the case that Mz/Mw is larger than 60, the deviation on the high molecular weight side in the distribution of the molecular weight is larger, resulting in an increase of the viscosity so that the dispersion and blending into each formulation becomes difficult. On the viewpoint, Mz/Mw may preferably be 60 or smaller and more preferably be 50 or smaller.

Further, in the case of the hair cleanser composition, as Mz/Mw is smaller than 5, the duration of the ruly style and the effect of suppressing the tabaco odor and cooking odor may possibly be insufficient, it is 5 or larger, preferably 15 or larger, more preferably 20 or larger and most preferably 30 or larger. In the case that Mz/Mw is larger than 60, the deviation on the high molecular weight side in the distribution of the molecular weight is larger, resulting in an increase of the viscosity so that the dispersion and blending into each formulation becomes difficult. On the viewpoint, Mz/Mw may preferably be 60 or smaller and more preferably be 50 or smaller.

In the case of the body cleanser composition, as Mz/Mw is smaller than 5, the duration of moisture feeling and the effect of suppressing the tabaco odor and cooking odor may possibly be insufficient. Thus, Mz/Mw is 5 or larger, preferably 15 or larger, more preferably 20 or larger, and most preferably 30 or larger. In the case that Mz/Mw is larger than 60, the deviation on the high molecular weight side in the distribution of the molecular weight is larger, resulting in an increase of the viscosity so that the dispersion and blending into each formulation becomes difficult. On the viewpoint, Mz/Mw may preferably be 60 or smaller and more preferably be 50 or smaller.

According to a preferred embodiment, in the gel permeation chromatography, the chromatogram is obtained by an indicative refractometer, is represented by the intensity of the refractive index and elution time and unsymmetrical with respect to the right and left sides. The tailing coefficient (TF) of the chromatogram calculated as follows satisfies 1.50≤TF≤5.0.

Figure 2:
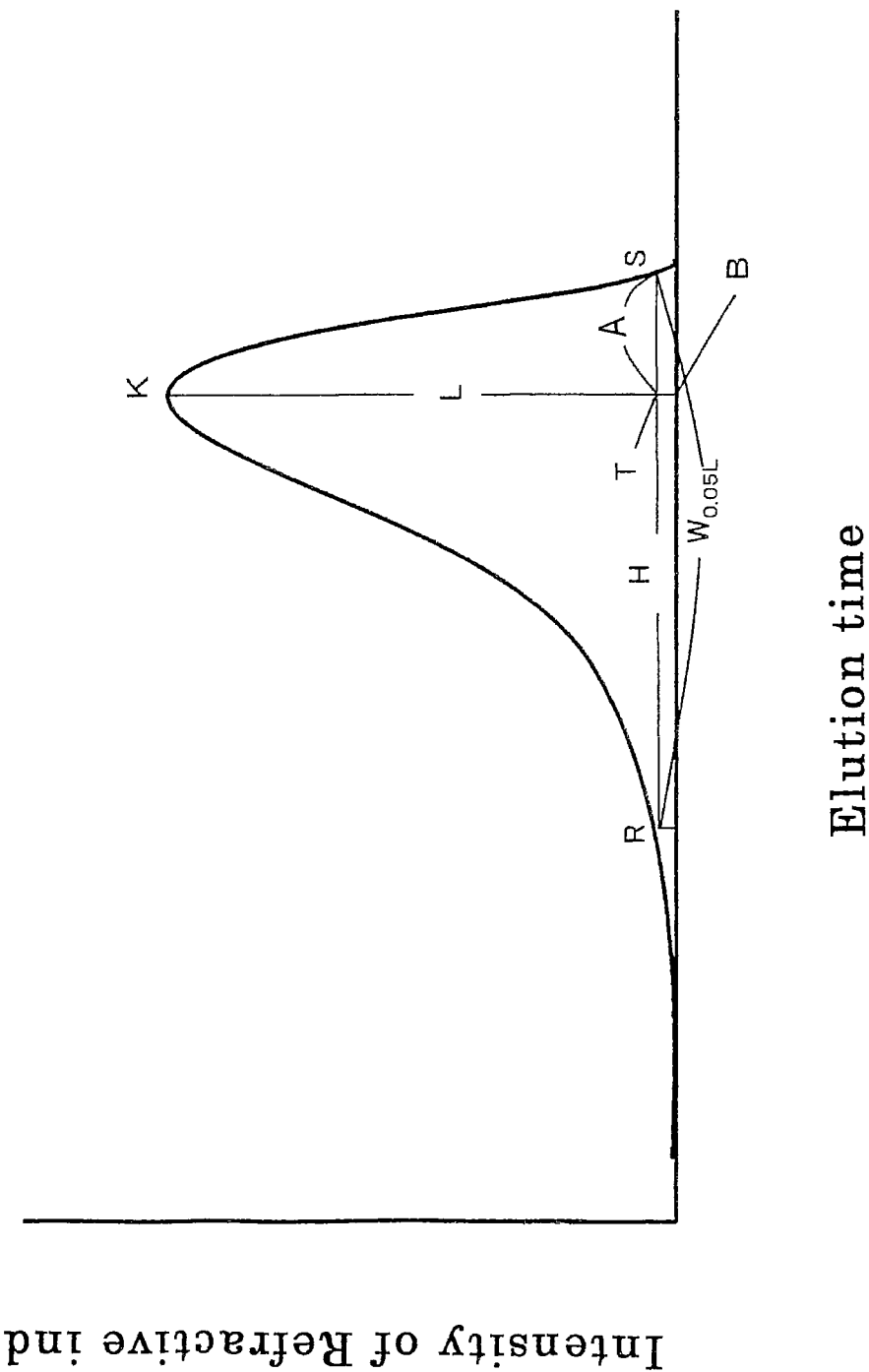
FIG. 2 is a model chromatogram for illustrating TF defined in the present invention.

The method of calculating TF will be described further, referring to the model diagram of the chromatogram of FIG. 2. The horizontal axis indicates the elution time and vertical axis indicates the intensity of refractive index obtained by the differential diffractometer. In the case that a sample solution is injected into and developed in a gel permeation chromatograph, the elution of molecules having the highest molecular weight is initiated first, and the elution curve is raised as an increase of the intensity of the refractive index. Thereafter, the elution curve goes down from the maximum point K where the intensity of the refractive index takes the maximum value.

Further, in the case that there is a plurality of the maximum points of the intensity of the refractive index of the chromatogram in the gel permeation chromatography of the inventive alkylene oxide derivative, the maximum point K is defined where the intensity of the refractive index is the highest among them. Further, in the case that there is a plurality of the maximum points having the same intensity of the refractive index, the maximum point K is defined as that having a longer elution time. Further, peaks derived from a developing solvent used for the gel permeation chromatography and peaks derived from deviation of the base line due to a column or system used are excluded.

(1) A perpendicular line is drawn from the maximum point K of the intensity of the refractive index to the base line B on the chromatogram, and L is assigned to the length.

(2) Among two points at which the intensity of the refractive index is L/20 on the chromatogram, point R is assigned to the point having a shorter elution time, and point S is assigned to the point having a longer elution time.

(3) T is assigned to a crossing point of a straight line H connecting the points R and S and the perpendicular line drawn from the maximum point K of the intensity of the refractive index to the base line B.

(4) "A" is assigned to a distance between the points S and T, and $W_{0.05L}$ is assigned to a distance between the points R and S.

$$TF = W_{0.05L}/2A \qquad (3)$$

$$1.5 \leq TF \leq 5.0 \qquad (4)$$

According to a preferred embodiment, TF satisfies 1.5≤TF≤5.0. As TF is made 1.5 or larger, the versatility of temperature of the antifoaming agent, lubricating property of the lubricant, styling performance of the hair cosmetic or softness of the hair tends to be improved. On the viewpoint, TF may preferably be made 2.0 or larger.

Further, as TF is larger, the deviation of the molecular weight distribution on the side of the high molecular weight becomes larger, so that the resultant increase of the viscosity is observed. As TF is larger than 5.0, the deviation of the molecular weight distribution on the side of the high molecular weight becomes larger, resulting in an increase of the viscosity so that the dispersion and blending into each formulation becomes difficult. On the viewpoint, TF may preferably be 5.0 or smaller and more preferably be 4.0 or smaller.

According to the present invention, the gel permeation chromatography (GPC) for obtaining M z/Mw and TF is performed as follows. A GPC101GPC dedicated system "SHODEX" (Trade mark) is used as the system, "SHODEX R1-71s" is used as the differential refractometer, and "SHODEX KF-G" is used as a guard column. Three columns of "SHODEX KF804L" are continuously equipped as the columns, the temperature of the columns is made 40° C., tetrahydrofuran is flown at a flowing rate of 1 ml/minute as a developing solvent, 0.1 ml of tetrahydrofuran solution of the thus obtained reaction product of a content of 0.1 weight percent is injected and "BORWIN GPC calculation program" is used to obtain the chromatogram represented by the intensity of the refractive index and elution time.

In the case that the alkylene oxide derivative of the present invention is produced, preferably, the following alkylene oxide are subjected to ring-opening addition under the presence of a complex metal cyanide catalyst (referred to as DMC catalyst below) as an initiator. In a reaction container, an initiator having at least one hydroxyl group in the molecule and the DMC catalyst are charged, and alkylene oxides are continuously or intermittently added under an inert gas atmosphere upon stirring to perform the addition polymerization. Alkylene oxides may be added under pressure or under ambient pressure.

At this time, although an average supply rate of alkylene oxides is not limited, it may preferably be changed depending on a charged amount of alkylene oxides. Specifically, provided that $V_1$ is assigned to a rate (supply amount per an unit time) during the supply of 5 to 20 wt % of a total supply amount of alkylene oxides, that $V_2$ is assigned to a rate during the supply of 20 to 50 wt % of the total supply amount of alkylene oxides, and that $V_3$ is assigned to a rate during the supply of 50 to 100 wt % of the total supply amount of alkylene oxides, it is preferred to adjust the average supply rates of alkylene oxides satisfying $V_1/V_2$=1.1 to 2.0 and $V_2/V_3$=1.1 to 1.5.

Further, the reaction temperature may preferably be made 50 to 150° C. and more preferably 70° C. to 110° C. In the case that the reaction temperature exceeds 150° C., the activity of the catalyst might be lost. In the case that the reaction temperature is lower than 50° C., the reaction rate and productivity are low.

As the initiator in the present invention includes compounds represented by the formula (1) in which Z has a carbon number of 1 to 24 and the number x of hydroxyl group(s) is 1 to 6 and the compounds with oxypropylene added thereto. As the initiator, for example, butanol, butyl propylene glycol, polyoxypropylene glycol, polyoxypropylene glyceryl ether or the like are listed. In the case that Z is $R^1$, as the initiator, it may be used a monovalent alcohol ($R^1OH$) having the hydrocarbon group having a carbon number of 1 to 24 represented by $R^1$.

Although it is not particularly limited a small amount of water content contained in the initiator and propylene oxide, the water contents contained in the initiator may preferably be 0.5 wt % or lower and contained in propylene oxide may preferably be 0.01 wt % or lower, respectively.

Although the used amount of the DMC catalyst is not particularly limited, it may preferably be 0.0001 to 0.1 wt % and more preferably be 0.001 to 0.05 wt % with respect to an amount of the generated alkylene oxide derivative. The DMC catalyst may be initially charged in batch or sequentially supplied in division into the reaction system. After the polymerization reaction, the composite metal complex catalyst is removed. The removal of the catalyst may be performed by known methods such as filtration, centrifugation or processing by means of a synthetic adsorption agent.

As the DMC catalyst used in the present invention, known catalysts may be used. For example, it may be represented by formula (8).

$$Md[M'y(CN)z]e(H_2O)f \cdot (R)g \qquad (8)$$

In the formula (8), M and M' represent metals, respectively, R represents an organic ligand, d, e, y and z are positive integers, respectively, which are changed depending on atomic values and ligand numbers of the metals, and f and g are positive integers, respectively, which are changed depending on the ligand numbers of the metals.

As the metal M, Zn(II), Fe(II), Fe(III), Co(II), Ni(II), Al(III), Sr(II), Mn(II), Cr(III), Cu(II), Sn(II), Pb(II), Mo(IV), Mo(VI), W(IV), W(VI) and the like are listed, and among them, Zn(II) is preferably used, As the metal M', Fe(II), Fe(III), C(II), CO(III), Cr(II), Cr(III), Mn(II), Mn(III), Ni(II), V(IV), V(V) and the like are listed, and among them, Fe(II), Fe(III), Co(II), and Co(III) are preferably used.

As the organic ligand R, an alcohol, ether, ketone, ester and the like are listed, and the alcohol is more preferred. Preferred organic ligands are of soluble in water, and specifically include t-butyl alcohol, n-butyl alcohol, iso-butyl alcohol, N, N-dimethyl acetoamide, ethylene glycol dimethyl ether (glyme), diethylene glycol dimethyl ether (diglyme) and the like. $Zn_3[Co(CN)_6]_2$ having tert-butyl alcohol as the ligand is particularly preferred.

(Antifoaming Agent)

The alkylene oxide derivative of the present invention can be used as an antifoaming agent.

The antifoaming agent of the present invention may be used as the alkylene oxide derivative shown in the formula (1) alone or as a formulation in which the alkylene oxide derivative is dissolved into an aqueous component for improving the dispersion in water used for aqueous system.

The aqueous component includes water, a lower alcohol such as ethyl alcohol, propyl alcohol or the like, and mixture of water and the lower alcohol. Although the blending ratio of water is not particularly limited, the concentration of the alkylene oxide derivative may preferably be 0.1 to 99 wt %. In the case that the concentration of the alkylene oxide derivative is lower than 0.1 wt %, the antifoaming property may be deteriorated. On the other hand, in the case that the concentration of the alkylene oxide derivative is larger than 99 wt %, the handleability may be deteriorated.

The antifoaming agent of the present invention may further optionally contain other components such as a known antifoaming agent such as an organic solvent, mineral oil, animal and plant oils or the like, a stabilizer, thickener, preservative or the like.

Although the applications of the antifoaming agent of the present invention are not particularly limited, it may be used for fermentation industry applications such as amino acid fermentation, carboxylic acid fermentation, enzyme fermentation, antibiotics fermentation or the like, paper and pulp production industry, construction industry, dye industry, staining industry, rubber industry, synthetic resin industry, ink industry, paint industry, fiber industry or the like.

In the case that the antifoaming agent of the present invention is used, although the blending ratio with respect to an aqueous medium required to be defoamed is not particularly limited, for example, it may normally be 0.0001 to 10 wt %, preferably be 0.0001 to 5 wt % and more preferably be 0.001 to 5 wt %, with respect to 100 wt % of the aqueous medium.

(Lubricant)

The alkylene oxide derivative of the present invention can be as a lubricant.

The lubricant of the present invention may be used as the alkylene oxide derivative shown by the formula (1) alone, or as a formulation in which the alkylene oxide derivative is dissolved into an aqueous component for improving the dispersion in water for use in aqueous system. The aqueous component includes water, a lower alcohol such as ethyl alcohol or propyl alcohol, and mixture of water and the lower alcohol.

As the lubricant of the present invention is water soluble and have superior lubricating and antifoaming properties, it may be used as cutting oil of water-containing system, lubricant for sliding planes, rolling oil, extraction oil, press oil, forging oil, metal processing oil used for processing such as polishing and cutting of an aluminum disk and silicon wafer, base oil used for an aqueous lubrication oil such as water-glycol system hydraulic oil or the like.

Further, into the lubricant of the present invention, it may be optionally added other components generally used in the lubricant including a cleaning dispersant, anti-oxidant, oily agent, emulsifier, extreme pressure agent, metal inactivating agent, anti-rust agent, viscosity improver, pour point depressant or the like.

(Cosmetic Base)

The alkylene oxide derivative of the present invention can be used for a cosmetic by blending it as a raw material. Particularly, in the case that it is blended in the hair cosmetic, particularly styling agent, the ruly style and finger passage are good, and it is possible to obtain set-preservative performance while soft feeling of hair is maintained. Further, in the case of a skin cosmetic, compatibility with skin upon application is good, thick feeling is obtained and the friction feeling during massage can be reduced.

The alkylene oxide derivative of the present invention is used as a feeling improver and styling agent in the cosmetic, and its concentration may preferably be 0.5 to 25 wt %. As the concentration of the alkylene oxide derivative in lower than 0.5 wt %, the sufficient results may not be obtained. On the viewpoint, the concentration of the alkylene oxide derivative may preferably be 0.5 wt % or higher and more preferably be 1 wt % or higher. Further, the concentration is higher than 25 wt %, sticky feeling is provided upon drying, which is unsuitable as a cosmetic.

The cosmetic of the present invention may be a hair cosmetic. Into the hair cosmetic, water and other additional components generally used and blended into the cosmetic may optionally be added, and the components include, for example, oily bases, surfactants, alcohols, moisturizers, high molecular•thickening•gelling agents, antioxidants, preservatives, fungicides, chelating agents, pH adjusting agents•acids•alkalis, ultraviolet light absorbers, whitening agents, solvents, exfoliating and dissolving agents of dead skin, antipruritic agents, anti-inflammatory agents, antiperspirants, refreshing agents, reducing•oxidizing agents, high molecular powders, vitamins and the derivatives, sugars and the derivatives, organic acids, inorganic powders, fragrances, pigments or the like.

Further, the cosmetic of the present invention may be a skin cosmetic. Into the skin cosmetic, water and other additional components generally used and blended into the cosmetic may optionally be added, and the components include, for example, oily bases, surfactants, alcohols, polyhydric alcohols, moisturizers, high molecular•thickening•gelling agents, antioxidants, preservatives, fungicides, chelating agents, pH adjusting agents•acids•alkalis, ultraviolet light absorbers, whitening agents, solvents, exfoliating and dissolving agents of dead skin, antipruritic agents, anti-inflammatory agents, antiperspirants, refreshing agents, reducing•oxidizing agents, high molecular powders, vitamins and the derivatives, sugars and the derivatives, organic acids, inorganic powders, fragrances, pigments or the like.

(Hair Cleanser Composition)

Provided that 100 mass % is assigned to the total amount of the hair cleanser composition of the present invention, the content of (A) component is 0.01 to 20 mass %, may preferably be 0.1 to 15 mass % and most preferably be 0.5 to 10 mass %. In the case that the content of (A) component is too low, the duration of the ruly style and the effect of suppressing the tabaco odor and cooking odor may be deteriorated, and in the case that the content of (a) component is too high, the rinsing property of the cleansing agent may be deteriorated.

(Component (B): Anionic Surfactant)

(B) component used in the present invention is an anionic surfactant blended in the hair cleanser composition for imparting foaming power and cleansing power.

The anionic surfactant includes, for example, alkyl sulfate ester salts, polyoxyethylene alkyl ether sulfate salts, alkyl amide ether sulfate salts, polyoxyethylene amide ether sulfate salts, polyoxyethylene alkyl ether acetate salts, alkyl phosphate salts, polyoxyethylene alkyl ether phosphate salts, salts of α-olefin sulfonic acids, salts of higher fatty acids, salts of N-acylamino acids, salt of N-acyl isethionic acid, N-acyl methyl taurate salt, salts of N-acyl polypeptides, salts of alkyl sulfo-succinic acids or the like.

Among them, alkyl sulfate ester salts, polyoxyethylene alkyl ether sulfate salts, N-acyl methyl taurate salt and salts of N-acyl amino acids are preferred, and salts of N-acyl methyl taurate and N-acyl amino acids are more preferred. The number of carbons in the alkyl group or acyl group may preferably be 10 to 18 and more preferably be 12 to 14, on the viewpoint of cleansing power and foaming power. Further, the alkyl group and acyl group may be derived from any of a saturated fatty acid, unsaturated fatty acid and mixed fatty acids which are the mixture of them. The mixture of the fatty acids includes, for example, coconut acid fatty acid and palm oil fatty acid and the like.

The counterions of them include, for example, alkali metal salts, alkali earth metal salts, ammonium salts, alkanol amine salts, amino acid salts and the like.

One or two or kinds selected from the anionic surfactants described above may be used as (B) component.

Provided that 100 mass % is assigned to the total amount of the hair cleanser composition, the content of (B) component is 1 to 50 mass %, preferably 3 to 30 mass % and most preferably 5 to 20 mass %, with respect to the total amount of the composition. In the case that the content of (B) component is too low, the viscosity, fineness of bubbles and foaming power may be deteriorated, and in the case that the content is too high, the amount of the bubbles may possibly be lowered.

(Component (C): Cationic Polymer)

The (C) component used in the present invention is a cationic polymer including homopolymer of dialkyl diallyl ammonium chloride, copolymer of dialkyl diallyl ammonium chloride and (meth)acrylate, copolymer of dialkyl diallyl ammonium chloride and (meth)acrylamide, polymethacryloyl oxyethyltrimethyl ammonium chloride, cationated cellulose, cationated starch, cationated guar gum, cationated tara gum, cationated locust beam gum, cationated xanthan gum, cationated fenugreek gum, copolymer of vinyl imidazolenium chloride and vinyl pyrrolidone, copolymer of hydroxy ethyl cellulose and dimethyl diallyl ammonium chloride, copolymer of vinyl pyrrolidone and dimethyl aminoethyl methacrylate, copolymer of polyvinyl pyrrolidone, alkylamino acrylate and vinyl caprolactam, copolymer of vinyl pyrrolidone and methacrylamide propyl-trimethyl ammonium chloride, copolymer of alkylacrylamide, acrylate and alkyl amino alkyl acrylamide and polyethylene glycol methacrylate, copolymer of adipic acid and dimethyl amino-hydroxypropyl-ethylene triamine and the like. In particular, cationated cellulose, cationated guar gum, cationated tara gum, homopolymer of dialkyl allyl ammonium chloride, and copolymer of dialkyl diallyl ammonium chloride and (meth)acrylamide are preferred. Further, (meth) acrylate means acrylate or methacrylate, and (meth)acrylic means acrylic or methacrylic.

The degree of cationization of the cationated polymer can be calculated based on measured values of N-content rates by Kjeldahl method or the like, and it is preferably be 0.2 to 3 meq/g and more preferably 0.5 to 2 meq/g. Further, "meq/g", which is a unit of the degree of cationization, means a milli equivalent of N-cationic group per 1 g of a sample.

Further, the weight average molecular weight of the cationated polymer may preferably be in a range of 100,000 to 3,000,000 and more preferably be in a range of 400,000 to 2,000,000.

The specific examples of such cationated polymers include, for example, LEOGARD LP, GP and MGP (supplied by LION Corporation), UCARE LR-30M, JR-400, JR-30M (supplied by The Dow chemical company), Labor Gum CG-M, CG-M7 and CG-MSM (supplied by Sumitomo Dainippon Pharma corporation), N-Hance 3000 (supplied by Harcules Japan Incorporated) and the like.

As the (C) component, one or two or more kinds selected from the cationated polymers described above may be used.

Provided that 100 mass % is assigned to the total amount of the hair cleanser composition, the content of the (C) component is 0.01 to 3.0 mass %, preferably 0.1 to 2 mass % and most preferably 0.3 to 1 mass %, with respect to the total amount of the composition. In the case that the content of the (C) component is too low, the viscosity and foaming power may be deteriorated, and in the case that the content is too high, the discharge from a container may be deteriorated, the amount of foam may be lowered or the rinsing property of the cleanser may possibly be deteriorated.

The hair cleanser composition of the present invention contains a solvent in addition to (A) to (C) components as described above. Such solvent includes water and lower alcohols. As the water, for example, purified water, ion exchange water, distilled water, RO (Reverse Osmosis) water, tap water, water for industrial use and the like are listed. As the lower alcohol, for example, ethanol, 2-propanol, ethylene glycol and the like are listed. Among the solvents, water such as purified water is particularly preferred.

The solvent is used in an amount for adjusting the contents of the respective components (A) to (C) and optionally contained other components at predetermined contents. Specifically, the content of the solvent in the present invention is 30 to 99 mass %, preferably 50 to 95 mass %, and most preferably 65 to 90 mass %, with respect to the total amount of the composition.

The hair cleanser composition of the present invention can be produced by a conventional method. The mode of the hair cleanser composition of the present invention can be appropriately selected as liquid, gel or the like. Further, the mode of utilization is not limited, and it may be used as a hair shampoo, rinse-in-shampoo or the like.

According to the hair cleanser composition of the present invention, additives commonly used in the cleanser may be blended as far as the performance of the present invention is not lost. For example, it is possible to blend a pearlizing agent such as glycol distearate to provide pearl-like liquid shampoo having glossy tone and emulsified color.

Into the hair cleanser composition of the present invention, water and other additional components generally used and blended into the cosmetic may optionally be added, and the components include, for example, oily bases, surfactants, alcohols, moisturizers, high molecular•thickening•gelling agents, antioxidants, preservatives, fungicides, chelating agents, pH adjusting agents•acids•alkalis, ultraviolet light absorbers, whitening agents, solvents, exfoliating and dissolving agents of dead skin, antipruritic agents, anti-inflammatory agents, antiperspirants, refreshing agents, reducing•oxidizing agents, high molecular powders, vitamins and the derivatives, sugars and the derivatives, organic acids, inorganic powders, fragrances, pigments or the like.

(Body Cleanser Composition)

Provided that the 100 mass % is assigned to the total amount of the body cleanser composition, the content of the component (A) described above is 0.01 to 20 mass %, preferably 0.1 to 15 mass %, and most preferably 0.5 to 10 mass %. In the case that the content of the component (A) is too low, the duration of the moisture effect and the effect of suppressing the tabaco odor and cooking odor may be deteriorated, and in the case that the content is too high, the rinsing property of the cleanser may possibly be deteriorated.

(Component (D): Anionic Surfactant)

The component (D) used in the present invention is a surfactant blended for imparting foaming or cleansing power to the body cleanser composition, and is an anionic surfactant.

The anionic surfactant includes, for example, higher fatty acids, salts of alkyl sulfate esters, salts of polyoxyethylene alkyl ether sulfates, salts of alkyl amide ether sulfates, salts of polyoxyethylene amide ether sulfate esters, salts of polyoxyethylene alkyl ether acetates, salts of alkyl phosphates, salts of polyoxyethylene alkyl ether phosphates, $\alpha$-olefin sulfonates, salts of higher fatty acids, salts of N-acyl amino acids, N-acyl isethionate salt, N-acyl methyl taurate salt, N-acyl polypeptide salts, salt of alkyl sulfosuccinate and the like.

Among them, salts of the higher fatty acids, salts of alkyl sulfate esters, salts of polyoxyethylene alkyl ether sulfates, N-acyl methyl taurate salt and N-acyl amino acid salts are preferred, and N-acyl methyl taurate salt and N-acyl amino acid salt are more preferred. The number of carbons of the alkyl groups or acyl groups may preferably be 10 to 18 and more preferably be 12 to 14, on the viewpoint of cleansing and foaming powers. Further, the alkyl and acyl groups may be derived from a saturated fatty acid, unsaturated fatty acid or the mixture of the fatty acids. The mixture of the fatty acids includes, for example, coconut oil fatty acid or palm oil fatty acid.

The counter ions include, for example, salts of an alkali metals, alkali earth metals, ammoniums, alkanol amines, amino acids and the like.

Specific examples of the anionic surfactants include, for example, sodium lauryl ether sulfate, sodium methyl cocoyl taurate, sodium cocoyl glutamate, sodium lauroyl methyl alaninate.

One kind or two or more kinds selected from the surfactants as described above may be used as the component (D).

Provided that 100 mass % is assigned to the total amount of the body cleanser composition, the content (total amount) of the component (D) as described above is 0.1 to 50 mass %, preferably 3 to 35 mass %, and most preferably 5 to 30 mass %. In the case that the content of the (D) component is too low, the feeling after the rinsing or viscosity of the formulation may be deteriorated, and in the case that the content is too high, the moisture feeling may possibly be deteriorated.

(Component (E): Polyhydric Alcohol)

The component (E) used in the present invention is a polyhydric alcohol. The number of carbons of the polyhydric alcohol may preferably be 3 to 6 and the valence may preferably be 2 to 4. The polyhydric alcohol includes, for example, polyhydric alcohols such as glycerin, pentylene glycol, 1,3-buthylene glycol, erythritol, propylene glycol, dipropylene glycol, diglycerin, hexylene glycol, isoprene glycol and the like. Among them, glycerin, 1,3-butylene glycol, propylene glycol and diglycerin are preferred.

Provided that 100 mass % is assigned to the total amount of the body cleanser composition, the content of the component (E) as described above is 0.1 to 50 mass %, preferably 0.5 to 40 mass % and most preferably 1 to 25 mass %, with respect to the total amount of the composition. In the case that the content of the component (E) is too low, the moisture feeling on the skin may be deteriorated, and in the case that the content is too high, the rinsing property may possible be deteriorated.

The body cleanser composition of the present invention contains a solvent in addition to the components (A), (D) and (E) as described above. Such solvent includes water and lower alcohols. As the water, for example, purified water, ion exchange water, distilled water, RO (Reverse Osmosis) water, tap water, water for industrial use and the like are listed. As the lower alcohol, for example, ethanol, 2-propanol, ethylene glycol and the like are listed. Among the solvents, water such as purified water is particularly preferred.

The solvent is used in an amount for adjusting the contents of the respective components (A), (D) and (E) and optionally contained other components at predetermined contents. Specifically, the content of the solvent in the present invention is 30 to 99 mass %, preferably 50 to 95 mass % and most preferably 65 to 90 mass %, provided that 100 mass % is assigned to the total amount of the body cleanser composition.

The body cleanser composition of the present invention can be produced by a conventional method. The mode of the body cleanser composition of the present invention can be appropriately selected as liquid, gel or the like. Further, the mode of utilization is not limited, and it may be used as a body soap, cleansing agent or the like.

According to the body cleanser composition of the present invention, additives commonly used in the cleanser may be blended as far as the performance of the present invention is not lost. For example, it is possible to blend a pearlizing agent such as glycol distearate to provide pearl-like liquid body soap having glossy tone and emulsified color.

Into the body cleanser composition of the present invention, water and other additional components generally used and blended into the composition may optionally be added, and the components include, for example, oily bases, surfactants, alcohols, polyhydric alcohols, moisturizers, high molecular•thickening•gelling agents, antioxidants, preservatives, fungicides, chelating agents, pH adjusting agents•acids•alkalis, ultraviolet light absorbers, whitening agents, solvents, exfoliating and dissolving agents of dead skin, antipruritic agents, anti-inflammatory agents, antiperspirants, refreshing agents, reducing•oxidizing agents, high molecular powders, vitamins and the derivatives, sugars and the derivatives, organic acids, inorganic powders, fragrances, pigments or the like.

EXAMPLES (Examples of Alkylene Oxide Derivatives)

The present invention will be described below, referring to inventive and comparative examples.

(Synthesis of a Catalyst of a Complex of a Composite Metal Cyanide)

Into 2.0 ml of aqueous solution containing 2.1 g of zinc chloride, 15 ml of aqueous solution containing 0.84 g of potassium hexacyano cobaltate $K_3Co(CN)_6$ was added dropwise at 40° C. for 15 minutes while stirring. After the termination of the addition dropwise, 16 ml of water and 16 g of tert-butyl alcohol were added and the temperature was elevated to 70° C., followed by stirring for 1 hour. After the cooling to room temperature, filtration (first-time filtration) was performed to obtain solid. 14 ml of water and 8.0 g of tert-butyl alcohol were added to the solid, followed by agitation for 30 minutes and filtration (second-time filtration) to obtain solid.

Further, 18.6 g of tert-butyl alcohol and 1.2 g of methanol were added to the solid again, followed by agitation for 30 minutes and filtration (third-time filtration) to obtain solid.

The thus obtained solid was dried at 40° C. under reduced pressure for 3 hours to obtain 0.7 g of catalyst of a complex of composite metal cyanide.

Synthetic Example 1: Synthesis of Compound 1 of the Inventive Example

Into a 5-liter autoclave equipped with a thermometer, pressure gauge, security valve, tube for blowing nitrogen gas, agitator, vacuum discharge tube, cooling coil and vacuum jacket, 100 g of butyl propylene glycol and 0.04 g of the complex catalyst of the composite metal cyanide were charged. After replacement with nitrogen, the temperature was elevated to 110° C. 132 g of propylene oxide was charged under condition of 0.3 MPa or lower through the tube for blowing nitrogen gas, and it was measured the change of pressure and temperature in the reaction bath over time. After 3 hours, the pressure in the reaction bath was rapidly lowered. Thereafter, the temperature in the reaction bath was maintained at 110° C., and 1494 g of propylene oxide and 1258 g of ethylene oxide were gradually added dropwise through the tube for blowing nitrogen gas under condition of 0.5 MPa or lower. After the termination of the addition, the reaction was performed at 110° C. for 1 hour and the treatment under reduced pressure was performed at 75 to 85° C. for 1 hour, followed by the filtration. The thus obtained compound 1 was subjected to measurement by gel permeation chromatography.

Further, butyl propylene glycol was supplied by Nippon Nyukazai Co. Ltd., propylene oxide was supplied by Sumitomo Chemical Limited, and ethylene oxide was supplied by Nippon Shokubai., Co. Ltd.

Synthetic Examples 2 to 13: Synthesis of Compounds 2 to 6 of Inventive Examples, Compounds A1 to A4 of Inventive Examples, Compounds 1 and 2 of Comparative Examples 1 and 2, and Compound A'1 of Comparative Example The compounds were synthesized according to the same procedure as that of the synthetic example 1, except the starting materials, numbers of moles added of propylene oxide and ethylene oxide and random ratios. The thus obtained compounds 2 to 6 of the inventive examples, compounds A1 to A4 of the inventive examples, compounds 1 and 2 of the comparative examples and compound A'1 of the comparative example were subjected to measurement by gal permeation chromatography.

Synthetic Examples 14 and 15: Compound 3 of Comparative Example and Compound A'2 of comparative example Into a 5-liter autoclave equipped with a thermometer, pressure gauge, security valve, tube for blowing nitrogen gas, agitator, vacuum discharge tube, cooling coil and vacuum jacket, 100 g of butyl propylene glycol and 6.0 g of potassium oxide as a catalyst were charged. After replacement with nitrogen, the temperature was elevated to 110° C. Mixture of 1626 g of propylene oxide and 1258 g of ethylene oxide was gradually added dropwise under condition of 0.5 MPa or lower through the tube for blowing nitrogen gas. After the addition was terminated, the reaction was continued at 110° C. for 1.5 hours, the pressure reduction treatment was performed at 75 to 85° C. for 1 hour, and the reaction product was transferred into a 5-liter eggplant flask, rapidly neutralized with 1N hydrochloric acid, and subjected to dehydration under nitrogen gas pressure and filtration.

The values of Mz/Mw and TF calculated from the chromatograms of the synthetic examples 1 to 9 as well as the characteristics of the compounds were shown in table 1. Further, the hydroxyl value was measured based on JIS K-1557-1, and molecular weight was calculated from the hydroxyl value.

TABLE 1

| | Inventive Compound 1 | Inventive Compound 2 | Inventive Compound 3 | Inventive Compound 4 | Inventive Compound 5 | Inventive Compound 6 | Comparative Compound 1 | Comapartive Compound 2 | Comparative Compound 3 |
|---|---|---|---|---|---|---|---|---|---|
| Mz/Mw | 42.3 | 32.1 | 48.9 | 24.8 | 43.3 | 40.2 | 49.3 | 10.8 | 1.04 |
| TF | 3.01 | 2.89 | 3.45 | 2.32 | 3.16 | 3.07 | 3.21 | 1.43 | 0.85 |
| Molecular weight (Calculated from hydroxyl value) | 4,008 | 3,243 | 2,948 | 3,042 | 2,711 | 5,782 | 4,069 | 482 | 3,507 |
| Carbon bone structure | butanol | butanol | butanol | butanol | glycerin | sorbitol | butanol | butanol | butanol |
| Number a of moles added of PO a | 4 | 0 | 4 | 4 | 3 | 2 | 4 | 2 | 0 |
| Number b of moles added of PO b | 34 | 30 | 36 | 21 | 5 | 10 | 56 | 2 | 38 |
| Number c of moles added of EO c | 37 | 30 | 10 | 35 | 8 | 6 | 10 | 4 | 37 |
| a + b + c | 75 | 60 | 50 | 60 | 16 | 18 | 70 | 8 | 75 |
| b + c | 71 | 60 | 46 | 56 | 13 | 16 | 66 | 6 | 75 |
| random ratio x | 0.95 | 1.00 | 0.92 | 0.93 | 0.83 | 0.89 | 0.94 | 0.75 | 1.00 |

(Property as Antifoaming Agent)

The antifoaming test was performed for evaluating the antifoaming property of the alkylene oxide derivatives of the synthetic examples 1 to 9. Saponin was diluted with tap water to produce 0.04% aqueous solution of saponin, into which the alkylene oxide derivative was added to a content of 125 ppm. 200 ml of the thus obtained sample was charged into 1000 ml graduated cylinder, and air bubbling was performed for 10 minutes at 100 ml/min, while the aqueous solution was maintained at 20° C. The volume of the sample is defined as a volume from the bottom face of the graduated cylinder to the maximum height point of the bubbles, and the ratio of increase of the volume of the sample after the air bubbling was calculated. The ratio of increase of the volume is calculated according to the following formula, and as the ratio of increase of the volume is smaller, the antifoaming property is more excellent.

$$\text{Ratio of increase of volume}(\%) = \\ [(\text{volume of sample after air bubbling} - \text{volume of sample before air bubbling}\,(\text{ml})\,/\,\text{Volume of sample before air bubbling})(\text{ml})] \times 100$$

⊚: The increase ratio of the volume is lower than 110%, and the antifoaming property is excellent
○: The increase ratio of the volume is 110% or higher and lower than 200%, and antifoaming property is good.
Δ: The increase ratio of the volume is 200% or higher and lower than 300%, and antifoaming property is inferior.
×: The increase ratio of the volume is higher than 300%, and antifoaming property is inferior.

Further, the same experiments were performed at 40° C. and 60° C., respectively, and the results were shown in table 2.

(Performance as Lubricating Agent)

The friction coefficients were measured, for evaluating the lubricating performance of the alkylene oxide derivatives of the synthetic examples 1 to 9.

The test of the lubricating performance was carried out by SRV Lubricant and material test system (supplied by Optimal Corporation). The test was performed by means of ball/disk, and SUJ-2 was used for the respective test pieces. The friction coefficients (μ) were measured by using 5%, aqueous solution of the alkylene oxide derivatives, under the measurement conditions of a temperature of 50° C., load of 40N, amplitude of 1 mm and frequency of 50 Hz. The lubricating performance was evaluated based on the following standard. The results were shown in table 3.

⊚: Friction coefficient (μ) is 0.11 or lower.
○: Friction coefficient (μ) is higher than 0.11 and 0.12 or lower.
Δ: Friction coefficient (μ) is larger than 0.12 and 0.14 or lower.
×: Friction coefficient (μ) is higher than 0.14.

The antifoaming property in use as the lubricating agent was evaluated. 50 ml of the sample diluted into 5% aqueous solution was taken in 100 ml cylinder, which was agitated for 10 seconds, and then the time period until the bubbles disappeared was measured. The antifoaming property was evaluated based on the following standard. The results were shown in table 3.

⊚: Bubbles disappears in 15 seconds, and the antifoaming property is excellent.
○: Bubbles disappears in a time period longer than 15 seconds and of 30 seconds or shorter, and the antifoaming property was good.
Δ: Bubbles disappears in a time period longer than 30 seconds and of 60 seconds or shorter, and the antifoaming property is inferior.
×: Bubbles disappears in a time period longer than 60 seconds, and the antifoaming property is inferior.

(Styling Performance)

Curl retention test was performed for evaluating the styling performance of the alkylene oxide derivatives of the synthetic examples 1 to 9.

Styling mists were produced based on the compositions shown in table 4, using the alkylene oxide derivatives of the synthetic examples 1 to 9. The production method was as follows.

(1) Component A is weighed, and agitated and dissolved at 80° C. for 5 minutes.
(2) It is cooled to room temperature.
(3) Component B is added at room temperature and agitated until the components are uniformly mixed.

The thus obtained styling mist was filled in a mist spray bottle and 500 μL of the mist was then uniformly applied onto a hair bundle of 25 cm and 1 g. The hair bundle was rolled onto a rod having a diameter of 2 cm, dried under a constant temperature of 25° C. and a constant humidity of 40% over one night, and then removed from the rods. The length (L1) of the curled hair bundle was measured. The hair bundle was then hanged at constant conditions of a constant temperature of 25° C. and a constant humidity of 80%, and the length (L2) was measured again two hours later. The curl retention value (%) was calculated based on the following formula, and evaluated based on the following evaluation standard. The results were shown in table 5.

The curl retention value was calculated by substituting the length (L1) of the hair bundle and length (L2) of the hair bundle into the following formula. Further, as the curl retention value is nearer to 100, the degree of the change of the curled hair bundle is small and the performance of preserving the hair style under high humidity condition is excellent.

$$\text{Curl retention value}(\%) = ((25 - L2)/(25 - L1)) \times 100$$

(Standard for Evaluating Performance of Preserving Hair Style by Curl Retention)

⊚: Curl retention value is 85% or higher.
○: Curl retention value is 75% or higher and lower than 85%.
Δ: Curl retention value is 55% or higher and lower than 75%.
×: Curl retention value is lower than 55%.

(Evaluation of Cohesiveness of Hair Bundles, Finger Passage and Softness)

Functional evaluation by panelists was performed, for evaluating the cohesiveness of hair bundles, finger passage and softness of the alkylene oxide derivatives of the synthetic examples 1 to 9.

1000 μL was uniformly applied onto hair bundles each of 25 cm and 4 g, which were dried for 3 minutes by a drier. The hair bundles were stand still for 1 hour under constant conditions of a constant temperature of 25° C. and a constant humidity of 60%. As 10 panelists for functional evaluation contact the hairs at the finger tips, the cohesiveness of hair bundles, finger passage and softness were subjected to functional evaluation based on the following standard for evaluation. The results were shown in table 5.

(Evaluation of Cohesiveness after Styling)

The cohesiveness of hair bundles was evaluated based on the following standard.

⊚: 8 persons or more among 10 persons answered that the cohesiveness of hair tips was good.
○: 6 persons or more among 10 persons answered that the cohesiveness of the hair tips was good.
Δ: 4 persons or more among 10 persons answered that the cohesiveness of the hair tips was good.
×: 3 persons or less among 10 persons answered that the cohesiveness of hair tips was good.

(Evaluation of Finger Passage after Styling)

The finger passage through the hair was evaluated based on the following standard.

⊚: 8 persons or more among 10 persons answered that the finger passage was good.
○: 6 persons or more among 10 persons answered that the finger passage was good.
Δ: 4 persons of more among 10 persons answered that the finger passage was good.
x: 3 persons or less answered that the finger passage was good.

(Evaluation of Softness after Styling)

The softness of hair was evaluated based on the following standard.

⊚: 8 persons or more among 10 persons answered that it was appropriately soft.
○: 6 persons or more among 10 persons answered that it was appropriately soft.
Δ: 4 persons or more among 10 persons answered that it was appropriately soft.
x: 3 persons or less among 10 persons answered that it was appropriately soft.

TABLE 2

|  | Inventive Compound 1 | Inventive Compound 2 | Inventive Compound 3 | Inventive Compound 4 | Inventive Compound 5 | Inventive Compound 6 | Comparative Compound 1 | Comaparative Compound 2 | Comparative Compound 3 |
|---|---|---|---|---|---|---|---|---|---|
| Antifoaming property at 20° C. | ○ | ○ | ⊚ | ○ | ⊚ | ○ | ○ | X | X |
| Antifoaming property at 40° C. | ⊚ | ○ | ○ | ○ | ⊚ | ⊚ | Δ | X | Δ |
| Antifoaming property at 60° C. | ○ | ○ | ○ | ⊚ | ⊚ | ⊚ | Δ | Δ | ○ |

TABLE 3

|  | Inventive Compound 1 | Inventive Compound 2 | Inventive Compound 3 | Inventive Compound 4 | Inventive Compound 5 | Inventive Compound 6 | Comparative Compound 1 | Comaparative Compound 2 | Comparative Compound 3 |
|---|---|---|---|---|---|---|---|---|---|
| Lubricating property | ⊚ | ○ | ○ | ⊚ | ○ | ○ | Δ | X | X |
| Antifoaming property | ⊚ | ○ | ○ | ○ | ⊚ | ⊚ | Δ | X | Δ |

TABLE 4

|  | INCI | Composition |
|---|---|---|
| A | Water | 72.8 |
|  | Citric acid | 0.05 |
|  | Sodium citrate | 0.07 |
|  | PVP | 0.05 |
| B | Ethanol | 22 |
|  | Synthetic Examples 1 to 8 | 5.0 |

TABLE 5

|  | Inventive Compound 1 | Inventive Compound 2 | Inventive Compound 3 | Inventive Compound 4 | Inventive Compound 5 | Inventive Compound 6 | Comparative Compound 1 | Comaparative Compound 2 | Comparative Compound 3 |
|---|---|---|---|---|---|---|---|---|---|
| Styling performance | ⊚ | ⊚ | ○ | ⊚ | ○ | ○ | Δ | X | X |
| Cohesion after styling | ⊚ | ⊚ | ○ | ○ | ○ | ⊚ | Δ | X | X |
| Finger passage after styling | ⊚ | ○ | ○ | ○ | ⊚ | ○ | Δ | Δ | ○ |
| Softness after styling | ⊚ | ○ | ⊚ | ⊚ | ○ | ○ | ○ | Δ | ○ |

As can be seen from table 2, all the compounds 1 to 6 used in the inventive examples were excellent in antifoaming property at 20, 40 and 60° C.

As can be seen from table 3, all the compounds 1 to 6 used in the inventive examples were excellent in lubricating and antifoaming properties.

As can be seen from table 5, all the compounds 1 to 6 used in the inventive example were excellent in styling performance, cohesiveness of hairs, finger passage and softness after the styling.

Contrary to this, as can be seen from tables 2, 3 and 5, each of the compounds 1 to 3 of the comparative examples, which are not included in the alkylene oxide derivatives of the present invention, does not satisfy the antifoaming and lubricating properties, styling performance, cohesiveness, finger passage and softness after the styling at the same time.

(Cosmetic for Skin Use)

Preferred examples of formulated compositions of the skin cosmetic will be described below.

(Examples of Formulated Compositions of Skin Lotion)

The compound 1 of the inventive example described above and the following components were mixed in amounts shown in table 6 at room temperature (25° C.) until uniform mixture is obtained to produce toner. It was obtained liquid toner excellent in compatibility with skin upon application, feeling of thickness on contact and reduced friction feeling during massage.

TABLE 6

|  | Composition |
| --- | --- |
| Compound 1 of inventive example | 2 |
| Glycerin | 3 |
| Diglycerin | 3 |
| Dipropylene glycol | 2 |
| PEG-8 | 2 |
| Ethanol | 5 |
| Ascorbyl glucoside | 0.5 |
| Ethyl hexyl glycerin | 0.01 |
| Citric acid | 0.05 |
| Sodium citrate | 0.02 |
| PEG-60 hydrogenated castor oil |  |
| Tocopherol (d-δ-tocopherol) | 0.05 |
| EDTA-2Na | 0.01 |
| Water | residual part |
| Total | 100 |

(Examples of Formulated Compositions of Essence)

The compound 1 of the inventive example described above and the following components were mixed in amounts shown in table 7 at room temperature (25° C.) until uniform mixture was obtained, while preliminary mixed B is added to A, so that essence was prepared. It was thus obtained liquid essence excellent in compatibility with skin upon application, feeling of thickness, and reduced friction feeling during massage.

TABLE 7

|  |  | Composition |
| --- | --- | --- |
| A | Compound 1 of inventive example | 2 |
|  | Glycerin | 3 |
|  | 1,3-propane diol | 3 |
|  | PEG-150 | 2 |
|  | Xanthan gum | 0.05 |
|  | Carbomer | 0.05 |
|  | Phenoxy ethanol | 0.01 |
|  | Citric acid | 0.05 |

TABLE 7-continued

|  |  | Composition |
| --- | --- | --- |
|  | Sodium citrate | 0.02 |
|  | EDTA-2Na | 0.01 |
|  | Water | Residual part |
| B | Retinol palmitate | 0.02 |
|  | Polysorbate 80 | 3 |
|  | Fragrance | 0.1 |
| Total |  | 100 |

(Examples of Formulated Compositions of Emulsion)

The compound 1 of the inventive example 1 described above and following components were mixed in amounts shown in table 8. A and B phases were mixed respectively, heated at 75 to 80° C., mixed by means of a homo mixer, then cooled, and mixed with the addition of C until uniform mixture was obtained, so that emulsion was produced. It was thus obtained the liquid emulsion excellent in compatibility with skin upon application, feeling of thickness and reduced friction feeling during massage.

TABLE 8

|  |  | Composition |
| --- | --- | --- |
| A | Compound 1 of inventive example | 2 |
|  | 1,3-butane diol | 3 |
|  | Glycerin | 3 |
|  | Water | Residual part |
| B | Stearyl alcohol | 3 |
|  | Jojoba oil | 2 |
|  | Liquid paraffin | 2 |
|  | Ethylhexyl Palmitate | 2.5 |
|  | Triethylhexanoin | 3 |
|  | Polyoxyethylene sorbitan oleate | 1 |
|  | Glyceryl stearate | 1 |
| C | EDTA-2Na | 0.01 |
|  | Polyquaternium-51 | 0.05 |
|  | Phenoxy ethanol | 0.01 |
| Total |  | 100 |

(Examples of Formulated Compositions of Cream)

The compounds 1 of the inventive example described above and the following components were mixed in amounts shown in table 9, while A and B phases were mixed respectively, heated at 75 to 80° C., mixed by means of a homo mixer, cooled, and mixed with the addition of C until uniform mixture was produced, to prepare emulsion. It was thus obtained the emulsion excellent in compatibility with skin upon application, feeling of thickness and reduced friction feeling during massage.

TABLE 9

|  |  | Composition |
| --- | --- | --- |
| A | Composition 1 of inventive example | 2 |
|  | Glycerin | 3 |
|  | Carbomer | 0.1 |
|  | Water | Residual part |
| B | Behenyl alcohol | 3 |
|  | Cyclopentasiloxane | 4 |
|  | Hydrogenated polyisobutene | 5 |
|  | Ethyl hexyl palmitate | 4 |
|  | Hydrogenated lecithin | 0.5 |
|  | Polyoxyethylene sorbitan oleate | 2 |
|  | Glyceryl stearate | 2 |

TABLE 9-continued

|   |   | Composition |
|---|---|---|
| C | EDTA-2Na | 0.01 |
|   | Phenoxy ethanol | 0.01 |
| Total |   | 100 |

(Examples of Hair Cleanser Compositions)

Mz/Mw calculated from chromatograms and characteristics of the compounds 1A to 4 of the inventive examples and compounds A'1 and A'2 of the comparative examples are shown in table 10. Further, the hydroxyl values were measured based on JIS K-1557-1, and molecular weights were calculated from the hydroxyl values.

TABLE 10

|   | Compound A1 of inventive example | Compound A2 of inventive example | Compound A3 of inventive example | Compound A4 of inventive example | Compound A'1 of comparative example | Compound A'2 of comparative example |
|---|---|---|---|---|---|---|
| Mz/Mw | 42.3 | 58.9 | 24.8 | 43.3 | 49.3 | 1.04 |
| Molecular weight (Calculated from hydroxyl value) | 3,507 | 2,948 | 3,042 | 2,505 | 3,369 | 3,507 |
| Carbon bone structure | Butanol | Butanol | Butanol | Glycerin | Butanol | Butanol |
| Number a of moles added of PO a | 4 | 4 | 4 | 11 | 4 | 0 |
| Number b of moles added of PO b | 28 | 36 | 21 | 13 | 56 | 38 |
| Number c of moles added of EO c | 31 | 10 | 35 | 24 | 10 | 37 |
| a + b + c | 63 | 50 | 60 | 48 | 70 | 75 |
| b + c | 59 | 46 | 56 | 37 | 66 | 75 |
| b/c | 0.90 | 3.60 | 0.60 | 0.54 | 5.60 | 1.03 |
| random ratio x | 0.94 | 0.92 | 0.93 | 0.77 | 0.94 | 1.00 |

The respective hair cleanser compositions shown in tables 11 and 12 were produced and evaluated according to the following methods.

(Feeling of Smoothness During Rinsing)

The cleanser compositions produced in the inventive and comparative examples were used by healthy panelists, and functional evaluation was performed about the feeling during the rinsing. The feeling of smoothness during the rinsing was subjected to relative evaluation at three stages based on the following standard of evaluation points. The total of the points provided by the ten panelists was calculated and evaluated based on the following evaluation standard.

Standard for Evaluation Points
  3 points: The feeling during the rinsing is smooth
  2 points: The feeling during the rinsing is slightly smooth.
  3 points: The feeling during the rinsing is smooth.
Standard for Evaluation
  ◉: 25 points or higher
  ○: 20 points or higher and lower than 25 points
  Δ: lower than 20 points (Durability of Cohesiveness of Hair after Cleansing)

The cleanser compositions produced in the inventive and comparative examples were used by healthy 10 panelists, and dried by means of a dryer, and the functional evaluation about the cohesiveness of hair was performed three hours later after the cleansing, so that the duration of cohesiveness of hair was evaluated. It was subjected to relative evaluation at three stages based on the following standard of the evaluation points, and the total of the points provided by the ten panelists was calculated and evaluated based on the following evaluation standard.

Standard for Evaluation Points
  3 points: Hair 3 hours after the cleansing was cohesive.
  2 points: Hair 3 hours after the cleansing was slightly cohesive.
  1 point: Hair 3 hours after the cleansing was not cohesive
Standard for Evaluation
  ◉: 25 points or higher
  ○: 20 points or higher and lower than 25 points
  Δ: lower than 20 points (Effect of Suppressing Tabaco Odor and Cooking Odor)

5 grams of bundles of hairs were washed with 100% sodium lauryl sulfate and formulations of the inventive examples and formulations of comparative examples, respectively, dried by means of a dryer, and stood still in constant conditions of a constant temperature of 25° C. and constant humidity of 40% over one night. The bundles were stood still in a smoking room, in which two smokers were included, with an area of about 4 tatami mats over 15 minutes, taken out, dried and then stood still under constant conditions of a constant temperature of 25° C. and constant humidity of 40% over 30 minutes, so that hair samples were obtained.

The odor of each of the hair samples cleansed with the formulations of the inventive examples and comparative examples was compared with the hair sample cleansed with 10% sodium lauryl sulfate, and subjected to relative evaluation at 3 stages based on the following evaluation points by 10 panelists. The total of the points provided by 10 panelists was calculated and evaluated based on the following evaluation standard.

Standard for Evaluation Points
  3 points: The effect of suppressing the odor was observed.
  2 points: The effect of suppressing the odor was slightly observed.
  1 point: The effect of suppressing the odor was not observed.
Standard for Evaluation
  ◉: 25 points or higher
  ○: 20 points or higher and lower than 25 points
  Δ: lower than 20 points

TABLE 11

| | INCI | Inventive examples | | | | | |
|---|---|---|---|---|---|---|---|
| | | 1 | 2 | 3 | 4 | 5 | 6 |
| (A) | Compound A1 | 1.0 | 1.0 | 1.0 | 1.0 | — | — |
| | Compound A2 | — | — | — | — | 1.0 | — |
| | Compound A3 | — | — | — | — | — | 1.0 |
| | Compound A4 | — | — | — | — | — | — |
| (A') | Comparative Compound A'1 | — | — | — | — | — | — |
| | Comparative Compound A'2 | — | — | — | — | — | — |
| | PEG/PPG/polybutylene glycol-8/5/3 glycerin | — | — | — | — | — | — |
| | PEG/PPG-2000/200 copolymer | — | — | — | — | — | — |
| (B) | Sodium Lauryl sulfate | 10 | — | — | — | — | — |
| | Sodium Laureth sulfate | — | 10 | — | — | — | — |
| | Sodium methyl cocoyl taurate | — | — | 10 | — | 10 | 10 |
| | Sodium Lauroyl Methylaminopropionate | — | — | — | 10 | — | — |
| (C) | Polyquaternium-10 | 0.50 | 0.50 | 0.50 | 0.50 | 0.50 | 0.50 |
| Other | Ciratic acid | 0.40 | 0.40 | 0.40 | 0.40 | 0.40 | 0.40 |
| | (Acrylic acid/Acrylic stearyl) copolymer | — | — | — | — | — | — |
| | Water | | | residual part | | | |
| | total | | | 100 | | | |
| Evaluation | Smmoth feeling after rinsing | ○ | ○ | ◎ | ◎ | ◎ | ○ |
| | Duration of cohesivenss of hairs after cleansing | ○ | ○ | ◎ | ◎ | ○ | ○ |
| | Effect of suppresing tabaco odor and cooking odor | ◎ | ◎ | ◎ | ◎ | ○ | ○ |

TABLE 12

| | INCI | Inv. Ex. | Comparative examples | | | |
|---|---|---|---|---|---|---|
| | | 7 | 1 | 2 | 3 | 4 |
| (A) | Compound A1 | — | — | — | — | — |
| | Compound A2 | — | — | — | — | — |
| | Compound A3 | — | — | — | — | — |
| | Compound A4 | 1.0 | — | — | — | — |
| (A') | Comparative Compound A'1 | — | 1.0 | — | — | — |
| | Comparative Compound A'2 | — | — | 1.0 | — | — |
| | PEG/PPG/polybutylene glycol-8/5/3 glycerin | — | — | — | 1.0 | — |
| | PEG/PPG-2000/200 copolymer | — | — | — | — | 0.24 |
| (B) | Sodium Lauryl sulfate | — | — | — | — | — |
| | Sodium Laureth sulfate | — | — | — | — | — |
| | Sodium methyl cocoyl taurate | 10 | 10 | 10 | 10 | 10 |
| | Sodium Lauroyl Methylaminopropionate . . . | — | — | — | — | — |
| (C) | polyquaternium-10 | 0.50 | 0.50 | 0.50 | 0.50 | 0.50 |
| Other | Ciratic acid | 0.40 | 0.40 | 0.40 | 0.40 | 0.40 |
| | (Acrylic acid/Acrylic stearyl) copolymer | — | — | — | — | 0.24 |
| | Water | | | | | |
| | Total | | | | | |
| Evaluation | Smmoth feeling after riinsing | ○ | ○ | ○ | ○ | ○ |
| | Duration of cohesivenss of hairs after cleansing | ○ | Δ | Δ | Δ | ○ |
| | Effect of suppresing tabaco odor and cooking odor | ◎ | Δ | Δ | Δ | Δ |

As can be seen from tables 11 and 12, all the inventive examples 1 to 7 are excellent in feeling of smoothness during the rinsing, duration of cohesiveness of hairs after the cleansing and effect of suppressing the tabaco odor and cooking odor.

Contrary to this, as can be seen from table 12, each of the comparative examples 1 to 4, which are not included in the alkylene oxide derivative of the present invention, does not satisfy all of the feeling of smoothness during the rinsing, duration of cohesiveness of hairs after the cleansing and the effect of suppressing the tabaco odor and cooking odor at the same time.

That is, according to the comparative example 1, as it was used the comparative compound A'1 in which b/c exceeds 5, the duration of cohesiveness of hairs after the cleansing and the effect of suppressing tabaco odor and cooking odor were inferior.

According to the comparative example 2, as it was used the compound A'2 of the comparative example in which Mz/Mw was low and a=0, the duration of cohesiveness of hairs after the cleansing and the effect of suppressing the tabaco odor and cooking odor were inferior.

According to the comparative example 3, as it was used a different kind of compound, the duration of cohesiveness of hairs after the cleansing and the effect of suppressing the tabaco and cooking odor was inferior.

According to the comparative example 4, it was used a different kind of compound, the effect of suppressing the tabaco odor and cooking odor was inferior.

(Examples of Body Cleanser Composition)

Mz/Mw calculated from the chromatograms and characteristics of the compounds A1 to A4 of the inventive examples and compounds A'1 and A'2 of the comparative examples are shown in table 13. Further, the hydroxyl values were measured based on JIS K-1557-1 and the molecular weights were calculated from the hydroxyl values.

TABLE 13

|  | Compound A1 of inventive example | Compound A2 of inventive example | Compound A3 of inventive example | Compound A4 of inventive example | Compound A'1 of comparative example | Compound A'2 of comparative example |
|---|---|---|---|---|---|---|
| Mz/Mw | 42.3 | 58.9 | 24.8 | 43.3 | 49.3 | 1.04 |
| Molecular weight (Calculated from hydroxyl value) | 3,507 | 2,948 | 3,042 | 2,505 | 4,069 | 3,507 |
| Carbon bone structure | Butanol | Butanol | Butanol | Glycerin | Butanol | Butanol |
| Number a of moles added of PO a | 4 | 4 | 4 | 11 | 4 | 0 |
| Number b of moles added of PO b | 28 | 36 | 21 | 13 | 56 | 38 |
| Number c of moles added of EO c | 31 | 10 | 35 | 24 | 10 | 37 |
| a + b + c | 63 | 50 | 60 | 48 | 70 | 75 |
| b + c | 59 | 46 | 56 | 37 | 66 | 75 |
| b/c | 0.90 | 3.60 | 0.60 | 0.54 | 5.60 | 1.03 |
| random ratio x | 0.94 | 0.92 | 0.93 | 0.77 | 0.94 | 1.00 |

Further, the body cleanser compositions shown in tables 14 and 15 were prepared and evaluated according to the following method. Further, the units of the respective numerical values shown in tables 14 and 15 are "mass %".

(Feeling of Smoothness During Rinsing)

The cleanser compositions prepared in the inventive and comparative examples were used by 10 healthy panelists and subjected to functional evaluation on the feeling during the rinsing, so that the feeling of smoothness during the rinsing was subjected to relative evaluation at three stages based on the following standard for evaluation of points. The total of the points by the 10 panelists was calculated and evaluated based on the following evaluation standard.

Standard for Evaluation Points
 3 points: The feeling during the rinsing is smooth.
 2 points: The feeling during the rinsing is slightly smooth.
 1 point: The feeling during the rinsing is not smooth.
Evaluation Standard
 ⊚: 25 points or higher
 ○: 20 points or higher and lower than 25 points
 Δ: lower than 20 points (Duration of Moisture Feeling after Cleansing)

The cleanser compositions prepared in the inventive and comparative examples were used by 10 healthy panelists, and subjected to functional evaluation on moisturizing feeling 3 hours after the cleansing, so that the duration of moisture feeling was subjected to relative evaluation at three stages based on the following evaluation standard. The total of the points provided by 10 panelists was calculated and evaluated based on the following evaluation standard.

Standard for Evaluation Points
 3 points: The skin is moisturized three hours after the cleansing.
 2 points: The skin is slightly moisturized three hours after the cleansing.
 1 point: The skin is not moisturized three hours after the cleansing.
Evaluation Standard
 ⊚: 25 points or higher
 ○: 20 points or higher and lower than 25 points
 Δ: lower than 20 points (Effect of Suppressing Tabaco Odor and Cooking Odor)

Artificial leathers were cleansed with 10% sodium lauryl sulfate, formulations of the inventive examples and formulations of the comparative examples, respectively, dried by means of a dryer, and stood still under constant conditions of a constant temperature of 25° C. and humidity of 40% over one night. The leathers were stood still in a smoking room, in which two smokers were included, with an area of about 4 tatami mats over 15 minutes, taken out, dried and then stood still under constant conditions of a constant temperature of 25° C. and constant humidity of 40% over 30 minutes, so that samples were obtained.

The odor of each of the samples cleansed with the formulations of the inventive examples and comparative examples was compared with the sample cleansed with 10% sodium lauryl sulfate, and subjected to relative evaluation at 3 stages based on the following evaluation points by 10 panelists. The total of the points provided by the 10 panelists was calculated and evaluated based on the following evaluation standard.

Standard for Evaluation Points
 3 points: Effect of suppressing odor was observed.
 2 points: Effect of suppressing odor was slightly observed.
 1 point: Effect of suppressing odor was not observed.
Evaluation Standard
 ⊚: 25 points or higher
 ○: 20 points or higher and lower than 25 points
 Δ: lower than 20 points

TABLE 14

|  |  |  | Inventive examples | | | | | |
|---|---|---|---|---|---|---|---|---|
|  | INCI |  | 1 | 2 | 3 | 4 | 5 | 6 |
| (A) | Compound A1 |  | 1.0 | 1.0 | 1.0 | 1.0 | 1.0 | — |
|  | Compound A2 |  | — | — | — | — | — | 1.0 |
|  | Compound A3 |  | — | — | — | — | — | — |
|  | Compound A4 |  | — | — | — | — | — | — |
| (D) | Pottasium laurate |  | 8 | — | — | — | — | — |
|  | Pottasium miristate |  | 2 | — | — | — | — | — |
|  | Sodium Lauryl sulfate |  | — | 10 | — | — | — | — |
|  | Sodium Laureth sulfate |  | — | — | 10 | — | — | — |
|  | Sodium methyl cocoyl taurate |  | — | — | — | 10 | — | 10 |
|  | Sodium Lauroyl Methylaminopropionate |  | — | — | — | — | 10 | — |

TABLE 14-continued

|  | INCI | Inventive examples | | | | | |
|---|---|---|---|---|---|---|---|
|  |  | 1 | 2 | 3 | 4 | 5 | 6 |
| (E) Solvent | Glycerin | 2 | 2 | 2 | 2 | 2 | 2 |
|  | Hydroxyethyl cellulose | 0.50 | 0.50 | 0.50 | 0.50 | 0.50 | 0.50 |
|  | Citric acid | 0.40 | 0.40 | 0.40 | 0.40 | 0.40 | 0.40 |
|  | polyquaternium-7 | — | — | — | — | — | — |
|  | Water | Residual part | | | | | |
|  | Total | 100.0 | | | | | |
| Evaluation | Smmoth feeling during rinsing | ○ | ○ | ○ | ◎ | ◎ | ◎ |
|  | Duration of cohesivenss of hairs after cleansing | ○ | ○ | ○ | ◎ | ◎ | ○ |
|  | Effect of suppresing tabaco odor and cooking odor | ◎ | ◎ | ◎ | ◎ | ◎ | ○ |

TABLE 15

|  | INCI | Inv. Ex. | | Comparative Examples | | | |
|---|---|---|---|---|---|---|---|
|  |  | 7 | 8 | 1 | 2 | 3 | 4 |
| (A) | Compound A1 | — | — | — | — | — | — |
|  | Compound A2 | — | — | — | — | — | — |
|  | Compound A3 | 1.0 | — | — | — | — | — |
|  | Compound A4 | — | 1.0 | — | — | — | — |
| (A') | Comapative compound A'1 | — | — | 1.0 | — | — | — |
|  | Comparative compound A'2 | — | — | — | 1.0 | — | — |
|  | PEG/PPG/polybutylene glycol-8/5/3 glycerin | — | — | — | — | 1.0 | — |
|  | Polyoxypropylene (14) diglyceryl ether | — | — | — | — | — | 1.0 |
| (D) | Sodium methyl cocoyl taurate | 10 | 10 | 10 | 10 | 10 | 10 |
|  | Sodium Lauroyl Methylaminopropionate | — | — | — | — | — | — |
| (E) Solvent | Glycerin | 2 | 2 | 2 | 2 | 2 | 2 |
|  | PEG-12 dimethycone | — | — | — | — | — | 1 |
|  | Hydroxyethyl cellulose | 0.50 | 0.50 | 0.50 | 0.50 | 0.50 | 0.50 |
|  | Citric acid | 0.40 | 0.40 | 0.40 | 0.40 | 0.40 | 0.40 |
|  | polyquaternium-7 | — | — | — | — | — | 0.50 |
|  | Water | Residual part | | | | | |
|  | Total | 100.0 | | | | | |
| Evaluation | ~~Smmoth~~ Smooth feeling during rinsing | ○ | ○ | ○ | ○ | ○ | ○ |
|  | Duration of cohesivenss of hairs after cleansing | ○ | ○ | Δ | Δ | Δ | ○ |
|  | Effect of suppresing tabaco odor and cooking odor | ○ | ◎ | Δ | Δ | Δ | Δ |

As can be seen from tables 14 and 15, all the inventive examples 1 to 8 were excellent in feeling of smoothness during the rinsing, duration of moisture feeling after the cleansing and effect of suppressing tabaco odor and cooking odor.

Contrary to this, as can be seen from table 15, each of the comparative examples 1 to 4 does not satisfy all of the feeling of smoothness during the rinsing, duration of moisture feeling after the cleansing and effect of suppressing tabaco odor and cooking odor.

That is, according to the comparative example 1, as the comparative compound A'1 having b/c larger than 5 was added, the duration of moisture feeling after the cleansing and effect of suppressing tabaco odor and cooking odor were inferior.

According to the comparative example 2, as it was added the compound A'2 of the comparative example with a low Mz/Mw and a of 0, the duration of moisture feeling after the cleansing and effect of suppressing tabaco odor and cooking odor were inferior.

According to the comparative example 3, as different kind of compound was added, the duration of moisture feeling after the cleansing and effect of suppressing the tabaco and cooking odor were inferior.

According to the comparative example 4, as a different kind of compound was added, the effect of suppressing tabaco odor and cooking odor was inferior.

Preferred examples of formulations are shown below.

Inventive Example 9: Oil-In Body Soap (A Phase)
  Hydroxy ethyl cellulose: 0.5 mass %
  Water: residual part
(B Phase)
  Lauric acid: 10 mass %
  Myristic acid: 3 mass %
  Palmitic acid: 1 mass %
  48% KOH: 8 mass %
  Sodium cocoyl methyl taurate: 3 mass %
  Cocamidopropyl betaine: 1 mass %
(C Phase)
  Sorbeth-40 tetraoleate: 3 mass %
  Macadamia Ternifolia Seed Oil: 0.5 mass %
(D Phase)
  Compound A1 of the present invention: 2 mass %
Preparation Method:
  The A phase was agitated at 80° C. until uniform mixture was obtained. The B and C phases were sequentially added to the A phase and agitated at 80° C., respectively, until uniform mixture was obtained after each of the phases added. The mixture was cooled to room temperature, the D phase was then added, and agitated until consistent. The preparation was thus completed.

Results:

The feeling of smoothness during the rinsing, duration of moisture feeling after the cleansing and effect of suppressing tabaco and cooking odors were excellent.

Inventive Example 10: Face Wash Paste (A Phase)
- Laurie acid: 10 mass %
- Myristic acid: 8 mass %
- Palmitic acid: 2 mass %
- 48% KOH: 11 mass %
- Glyceryl stearate: 2 mass %
- Sorbitan stearate: 1 mass %
- Sodium methyl cocoyl taurate: 4 mass %
- Glycerin: 25 mass %

(B phase)
- Sodium citrate: 0.2 mass %
- Compound A1 of the present invention: 2 mass %
- Water: Residual part Preparation Method:

The A phase was agitated at 80° C. into uniform mixture. It was cooled to room temperature, the B phase was added thereto, followed by agitation into uniform mixture. The preparation was thus completed.

Results:

The feeling of smoothness during the rinsing, duration of moisture feeling after the cleansing and effect of suppressing tabaco odor and cooking odor were excellent.

Inventive Example 11: Pump Foamer (A Phase)
- Compound A1 of the present invention: 1 mass %
- Sodim cocoyl methyl taurate: 5 mass %
- Cocamidopropyl betaine: 4 mass %
- Cocamido DEA: 1 mass %
- Dilauric acid PEG-75: 1.5 mass %
- Glycerin: 10 mass %
- Water: Residual part Preparation Method:

The A phase was agitated into uniform mixture. The preparation was thus completed.

Results:

The feeling of smoothness during the rinsing, duration of moisture feeling after the cleansing and effect of suppressing tabaco odor and cooking odor were excellent.

Inventive Example 12: Cleansing Water (A Phase)
- Compound A1 of the present invention: 1 mass %
- PEG-8 (Caprylic acid/capric acid) glyceryl: 3 mass %
- Sodium laureth sulfate: 0.3 mass %
- Polysorbate 20: 1 mass %
- BG (Butylene glycol): 2 mass %
- Water: Residual part Preparation Method:

The A phase was agitated into uniform mixture. The preparation was thus completed.

Results:

The feeling of smoothness during the rinsing, duration of moisture feeling after the cleansing and effect of suppressing tabaco and cooking odors were excellent.

The invention claimed is:

1. An alkylene oxide derivative represented by formula (1), wherein a ratio Mz/Mw of a weight average molecular weight (Mw) and z average molecular weight (Mz) calculated from a chromatogram obtained by gel permeation chromatography measurement of said alkylene oxide derivative satisfies formula (2) below, $$Z-[O-(PO)_a-(PO)_b/(EO)_c]-H]_n \quad (1)$$

in the formula (1),
Z represents a residual group of a compound having a number of carbons of 1 to 24 and 1 to 6 hydroxyl groups wherein all the hydroxyl groups are excluded,
n represents a number of 1 to 6,
PO represents oxypropylene group,
EO represents oxyethylene group,
a and b represent numbers of moles added of said oxypropylene group PO, respectively,
c represents a number of moles added of said oxyethylene group EO,
a represents a number of 1 to 100, b represents a number of 1 to 100, c represents a number of 1 to 200, a+b+c≥10, and b/c=1/5~5/1,
$(PO)_b/(EO)_c$ indicates that said oxypropylene group PO and said oxyethylene group EO are randomly added, and
a random ratio x of said oxypropylene group PO and said oxyethylene group EO satisfies 0.1≤x≤1, $$5 \leq M_z/M_w \leq 60, \quad (2)$$

wherein Mz is calculated from said gel permeation chromatography measurement based on the following formula (7), $$Mz = \frac{\sum(M^3 \cdot N)}{\sum(M^2 \cdot N)} = \frac{\sum(C \cdot M^2)}{\sum(C \cdot M)} \quad (7)$$

in the formula (7), "N" represents a number of alkylene oxide derivative molecules, "M" represents a molecular weight of said alkylene oxide derivative, and "C" represents a concentration of said alkylene oxide derivative, and
the random ratio x is defined as follows:
x=(b+c)/(a+b+c)
wherein (a+b+c) represents a total of the numbers of moles added of PO and EO included in $-(PO)_a-(PO)_b/(EO)_c$, and
(b+c) represents a total of the numbers of moles added of PO and EO included in $-(PO)_b/(EO)_c$, in which PO and EO are randomly added.

2. The alkylene oxide derivative of claim 1, wherein a tailing coefficient (TF) calculated from said chromatogram satisfies formulas (3) and (4), $$TF = W_{0.05L}/2A \quad (3)$$

$$1.5 \leq TF \leq 5.0 \quad (4)$$

wherein an intensity of a refractive index is L/20 on said chromatogram at two points R and S, L is assigned to a length of a perpendicular line drawn from a maximum point K whose intensity of a refractive index on said chromatogram takes a maximum value to a base line B on said chromatogram, an elution time at the point R is shorter than an elution time at the point S, T is assigned to a crossing point of a straight line H connecting said point R and said point S and of said perpendicular line drawn from said maximum point K to said base line B, A is assigned to a distance between said point S and said crossing point T, and $W_{0.05L}$ is assigned to a distance between said point R and said point S.

3. The alkylene oxide derivative of claim 1, wherein said random ratio x satisfies 0.5≤x<1.

4. An antifoaming agent comprising the alkylene oxide derivative of claim 1.

5. A lubricant comprising the alkylene oxide derivative of claim 1.

6. A cosmetic base material comprising the alkylene oxide derivative of claim 1.

7. A hair cosmetic comprising the cosmetic base material of claim 6.

8. A skin cosmetic comprising the cosmetic base material of claim 6.

9. A hair cleanser composition comprising 0.01 to 20 mass % of (A) the alkylene oxide derivative of claim 1, 1 to 50 mass % of (B) an anionic surfactant, and 0.01 to 3 mass % of (C) a cationic polymer, based on the total amount of the hair cleanser composition.

10. A body cleanser composition comprising 0.01 to 20 mass % of (A) the alkylene oxide derivative of claim 1, 0.1 to 50 mass % of (D) an anionic surfactant, and 0.5 to 50 mass % of (E) a polyhydric alcohol, based on the total amount of the body cleanser composition.

* * * * *